(12) United States Patent
Carry et al.

(10) Patent No.: US 7,230,007 B2
(45) Date of Patent: Jun. 12, 2007

(54) DERIVATIVES OF 3-(GUANIDINOCARBONYL) HETEROCYCLE, METHODS OF PREPARATION AND INTERMEDIATES THEREOF, THEIR USE AS MEDICAMENTS, AND PHARMACEUTICAL COMPOSITIONS THEREFROM

(75) Inventors: Jean-Christophe Carry, Saint Maur des Fosses (FR); Gilles Doerflinger, Les Ulis (FR); Arielle Genevois-Borella, Thias (FR); Michel Evers, La Queue en Brie (FR); Alain Le Brun, Vigneux (FR); Jean-Paul Martin, Colombes (FR); Pascal Desmazeau, Tigery (FR); Serge Mignani, Chatenay-Malabry (FR); Heinz-Werner Kleemann, Bischofsheim (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 172 days.

(21) Appl. No.: 10/865,454

(22) Filed: Jun. 10, 2004

(65) Prior Publication Data

US 2005/0014758 A1   Jan. 20, 2005

Related U.S. Application Data

(60) Provisional application No. 60/497,281, filed on Aug. 22, 2003.

(30) Foreign Application Priority Data

Jun. 12, 2003   (FR) .................................. 03 07080

(51) Int. Cl.
*A61K 31/44* (2006.01)
*C07D 471/02* (2006.01)

(52) U.S. Cl. ...................................... 514/300; 546/113
(58) Field of Classification Search ............... 514/300; 546/113

See application file for complete search history.

(56) References Cited

FOREIGN PATENT DOCUMENTS

| DE | 19622222 A1 | 12/1997 |
|----|-------------|---------|
| EP | 0 622 356 A1 | 11/1994 |
| EP | 0 708 091 A1 | 4/1996 |
| EP | 0 708 091 A2 | 4/1996 |
| EP | 0 708 091 A3 | 7/1996 |
| EP | 0 972 767 A1 | 1/2000 |
| WO | WO 2004/007479 | 1/2004 |

OTHER PUBLICATIONS

U.S. Appl. No. 10/749,630 and U.S. Appl. No. 10/749,631.*
Akito, T. Novel Guanidine Derivative, Patent Abstracts of Japan, vol. 1998, No. 2, Jan. 30, 1998 and JP 09 278767 (Fujisawa Pharmaceut. Co. Ltd.)(Oct. 28, 1997).
Boivin, G. P. et al, Variant Form of Diffuse Corporal Gastritis in NHE2 Knockout Mice, Comparative Medicine, vol. 50, Issue 5(2000) pp. 511-515.
Masereel B et al, An overview of inhibitors of Na+/H exchanger, European Journal of Medicinal Chemistry, vol. 38, No. 6(Jun. 2003) pp. 547-554.
Schultheis P. J. et al, Targeted Disruption of the Murine Na+/H+ Exchanger Isoform 2 Gene Causes Reduced Viability of Gastric Parietal Cells and Loss of Net Acid Secretion, J. Clin. Invest., vol. 101, Issue 6, (1998)pp. 1243-1253.

* cited by examiner

*Primary Examiner*—Kamal A. Saeed
*Assistant Examiner*—Susannah L. Chung
(74) *Attorney, Agent, or Firm*—Jiang Lin; Lawrence L. Martin

(57) ABSTRACT

The present invention discloses and claims compounds of formula I

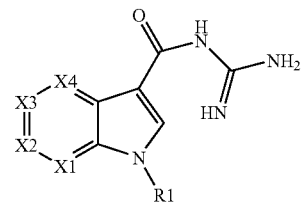

and their pharmaceutically acceptable salts, and methods of using said compounds of formula I, either alone or in combination with other medicaments, as antiarrhythmic medicaments with a cardioprotective component for prophylaxis or treatment of infarction, for the treatment of angina pectoris, and as inhibitors of pathophysiological processes associated with the development of ischemia-induced damage, in particular in the triggering of ischemia-induced cardiac arrhythmias and of heart failure. Pharmaceutical compositions comprising compounds of formula I or compounds of formula I in combination with one or more other medicaments and processes for the preparation of compounds of formula I are also disclosed and claimed.

9 Claims, No Drawings

DERIVATIVES OF 3-(GUANIDINOCARBONYL) HETEROCYCLE, METHODS OF PREPARATION AND INTERMEDIATES THEREOF, THEIR USE AS MEDICAMENTS, AND PHARMACEUTICAL COMPOSITIONS THEREFROM

This application claims the benefit of U.S. Provisional Application No. 60/497,281 filed Aug. 22, 2003, and the benefit or priority of French patent application number 0307080, filed Jun. 12, 2003, both of which are incorporated herein in their entirety by reference.

BACKGROUND OF THE INVENTION

FIELD OF THE INVENTION

The present invention relates to the novel compounds of formula I

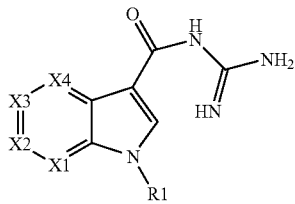

and their pharmaceutically acceptable salts. The compounds of the invention are suitable, for example, as antiarrhythmic medicaments with a cardioprotective component for infarction prophylaxis and infarction treatment and for the treatment of angina pectoris. They also inhibit in a preventive manner the pathophysiological processes associated with the development of ischemia-induced damage, in particular in the triggering of ischemia-induced cardiac arrhythmias and of heart failure.

SUMMARY OF THE INVENTION

The invention relates to compounds of formula I, in which $X_1$, $X_2$, $X_3$ and $X_4$ are, independently of one another, a nitrogen atom or a $CR_2$ group, in which at least one and at most two of X1, X2, X3 and X4 are nitrogen atoms;

$R_2$ is hydrogen, F, Cl, Br, I, alkyl having 1, 2, 3, 4, 5 or 6 carbon atoms, cycloalkyl having 3, 4, 5, 6 or 7 carbon atoms, polyfluoroalkyl having 1, 2, 3 or 4 carbon atoms, $SO_2$alkyl having 1, 2, 3, 4, 5 or 6 carbon atoms, NRaRb, hydroxyl, alkoxy having 1, 2, 3, 4, 5 or 6 carbon atoms, hydroxyalkyl having 1, 2, 3, 4, 5 or 6 carbon atoms or dialkylaminoalkyl with each alkyl having independently 1, 2, 3, 4, 5 or 6 carbon atoms;

R1 is aryl, alkyl having 1, 2, 3, 4, 5 or 6 carbon atoms, cycloalkyl having 3, 4, 5, 6 or 7 carbon atoms, polyfluoroalkyl having 1, 2, 3 or 4 carbon atoms, arylalkyl with alkyl having 1, 2, 3 or 4 carbon atoms, heteroarylalkyl with alkyl having 1, 2, 3 or 4 carbon atoms or heteroaryl, wherein said aryl or heteroaryl is optionally substituted by one or more substituents selected from the group consisting of alkyl having 1, 2, 3, 4, 5 or 6 carbon atoms, cycloalkyl having 3, 4, 5, 6 or 7 carbon atoms, F, Cl, Br, I, $NO_2$, $NH_2$, alkylamino with alkyl having 1, 2, 3, 4, 5 or 6 carbon atoms, NRaRb, alkylcarbonylamino having 1, 2, 3, 4, 5 or 6 carbon atoms, hydroxyl, alkoxy having 1, 2, 3, 4, 5 or 6 carbon atoms, $S(O)_nR_3$, $CO_2H$, alkoxycarbonyl having 1, 2, 3, 4, 5 or 6 carbon atoms, alkylcarbonyl having 1, 2, 3, 4, 5 or 6 carbon atoms, $CONH_2$, CONRaRb, alkylsulfonylamino with alkyl having 1, 2, 3, 4, 5 or 6 carbon atoms, cyano, polyfluoroalkyl having 1, 2, 3 or 4 carbon atoms, polyfluoroalkoxy having 1, 2 or 3 carbon atoms and $SO_3H$;

n is 0, 1 or 2;

Ra and Rb are, independently of one another, alkyl having 1, 2, 3, 4, 5 or 6 carbon atoms, or Ra and Rb form together with the nitrogen atom to which they are attached, a 5- or 6-membered heterocycle which can optionally comprise another heteroatom chosen from O, S or N;

$R_3$ is alkyl having 1, 2, 3, 4, 5 or 6 carbon atoms, alkylamino having 1, 2, 3, 4, 5 or 6 carbon atoms or $NH_2$;

and racemates, enantiomers and diastereomers and mixtures thereof, tautomers thereof and pharmaceutically acceptable salts thereof.

Preference is given to compounds of formula I in which:

$X_1$, $X_2$, $X_3$ and $X_4$ are, independently of one another, a nitrogen atom or a $CR_2$ group, wherein only one of X1, X2, X3 and X4 is a nitrogen atom;

$R_2$ is hydrogen;

R1 is aryl or heteroaryl,
wherein said aryl or heteroaryl is optionally substituted by one or more substituents selected from the group consisting of alkyl having 1, 2, 3, 4, 5 or 6 carbon atoms, cycloalkyl having 3, 4, 5, 6 or 7 carbon atoms, F, Cl, Br, I, $NO_2$, $NH_2$, alkylamino with alkyl having 1, 2, 3, 4, 5 or 6 carbon atoms, NRaRb, alkylcarbonylamino having 1, 2, 3, 4, 5 or 6 carbon atoms, hydroxyl, alkoxy having 1, 2, 3, 4, 5 or 6 carbon atoms, $S(O)_nR_3$, $CO_2H$, alkoxycarbonyl having 1, 2, 3, 4, 5 or 6 carbon atoms, alkylcarbonyl having 1, 2, 3, 4, 5 or 6 carbon atoms, $CONH_2$, CONRaRb, alkylsulfonylamino with alkyl having 1, 2, 3, 4, 5 or 6 carbon atoms, cyano, polyfluoroalkyl having 1, 2, 3 or 4 carbon atoms, polyfluoroalkoxy having 1, 2 or 3 carbon atoms and $SO_3H$;

n is 0, 1 or 2;

Ra and Rb are, independently of one another, alkyl having 1, 2, 3, 4, 5 or 6 carbon atoms, or Ra and Rb form together with the nitrogen atom to which they are attached, a 5- or 6-membered heterocycle which can optionally comprise another heteroatom chosen from O, S or N;

$R_3$ is alkyl having 1, 2, 3, 4, 5 or 6 carbon atoms, alkylamino having 1, 2, 3, 4, 5 or 6 carbon atoms or $NH_2$;

and racemates, enantiomers and diastereomers and mixtures thereof, tautomers thereof and pharmaceutically acceptable salts thereof.

More preference is given to compounds of formula I in which:

$X_1$, $X_2$, $X_3$ and $X_4$ are, independently of one another, a nitrogen atom or a $CR_2$ group, wherein only one of X1, X2, X3 and X4 is a nitrogen atom;

$R_2$ is hydrogen;

R1 is aryl or heteroaryl, which is selected from the group of pyridine, pyrimidine, pyrazine, thiazole, imidazole, quinoline, isoquinoline, cinnoline, quinazoline, naphthyridine, quinoxaline, benzothiazole, benzimidazole, indole, 7-azaindole and pyrrolo[2,3-d]pyrimidine, wherein said aryl or heteroaryl is optionally substituted by one or more substituents selected from the group consisting of alkyl having 1, 2, 3, 4, 5 or 6 carbon atoms, cycloalkyl having 3, 4, 5, 6 or 7 carbon atoms, F, Cl, Br, I, $NO_2$, $NH_2$, alkylamino with alkyl having 1, 2, 3, 4, 5 or 6 carbon atoms, NRaRb, alkylcarbonylamino having 1, 2, 3, 4, 5 or 6 carbon atoms, hydroxyl, alkoxy having 1, 2, 3, 4, 5 or 6 carbon atoms, $S(O)_n R_3$, $CO_2H$, alkoxycarbonyl having 1, 2, 3, 4, 5 or 6 carbon atoms, alkylcarbonyl having 1, 2, 3, 4, 5 or 6 carbon atoms, $CONH_2$, CONRaRb, alkylsulfonylamino with alkyl having 1, 2, 3, 4, 5 or 6 carbon atoms, cyano, polyfluoroalkyl having 1, 2, 3 or 4 carbon atoms, polyfluoroalkoxy having 1, 2 or 3 carbon atoms and $SO_3H$;

n is 0, 1 or 2;

Ra and Rb are, independently of one another, alkyl having 1, 2, 3, 4, 5 or 6 carbon atoms, or Ra and Rb form together with the nitrogen atom to which they are attached, a 5- or 6-membered heterocycle which can optionally comprise another heteroatom chosen from O, S or N;

$R_3$ is alkyl having 1, 2, 3, 4, 5 or 6 carbon atoms, alkylamino having 1, 2, 3, 4, 5 or 6 carbon atoms or $NH_2$;

and racemates, enantiomers and diastereomers and mixtures thereof, tautomers thereof and pharmaceutically acceptable salts thereof.

Particular preference is given to compounds of formula I in which:

$X_1$, $X_2$, $X_3$ and $X_4$ are, independently of one another, a nitrogen atom or a $CR_2$ group, wherein only one of X1, X2, X3 and X4 is a nitrogen atom;

$R_2$ is hydrogen;

R1 is phenyl or heteroaryl, which is selected from the group of pyridine, pyrimidine, pyrazine, thiazole, imidazole, quinoline, isoquinoline, cinnoline, quinazoline, naphthyridine, quinoxaline, benzothiazole, benzimidazole, indole, 7-azaindole and pyrrolo[2,3-d]pyrimidine, wherein said phenyl or heteroaryl is optionally substituted by one or more substituents selected from the group consisting of alkyl having 1, 2, 3, 4, 5 or 6 carbon atoms, $NH_2$, NRaRb, hydroxyl and $S(O)_n R_3$;

n is 2;

Ra and Rb are, independently of one another, alkyl having 1, 2, 3, 4, 5 or 6 carbon atoms;

$R_3$ is alkyl having 1, 2, 3, 4, 5 or 6 carbon atoms;

and racemates, enantiomers and diastereomers and mixtures thereof, tautomers thereof and pharmaceutically acceptable salts thereof.

In one embodiment of this invention, the compounds of formula I are defined as above and $X_1$, $X_2$, $X_3$ and $X_4$ represent, independently of one another, a nitrogen atom or a $CR_2$ group, wherein only one of X1, X2, X3 and X4 is nitrogen and preferably X1 is N and X2, X3 and X4 are CH.

In another embodiment of this invention, the compounds of formula I are defined as above and R2 represents independently hydrogen, chlorine, bromine, methyl or ethyl, preferably hydrogen.

In another embodiment of this invention, the compounds of formula I are defined as above and R1 represents aryl, preferably phenyl, or heteroaryl, preferably pyridine, pyrimidine, pyrazine, thiazole, imidazole, quinoline, isoquinoline, cinnoline, quinazoline, naphthyridine, quinoxaline, benzothiazole, benzimidazole, indole, 7-azaindole or pyrrolo[2,3-d]pyrimidine, more preferably pyridine, quinoline, isoquinoline or pyrrolo[2,3-d]pyrimidine. Aryl and heteroaryl may be substituted by one or more substituents selected from the group consisting of alkyl having 1, 2, 3, 4, 5 or 6 carbon atoms, cycloalkyl having 3, 4, 5, 6 or 7 carbon atoms, F, Cl, Br, I, $NO_2$, $NH_2$, alkylamino with alkyl having 1, 2, 3, 4, 5 or 6 carbon atoms, NRaRb, alkylcarbonylamino having 1, 2, 3, 4, 5 or 6 carbon atoms, hydroxyl, alkoxy having 1, 2, 3, 4, 5 or 6 carbon atoms, $S(O)_n R_3$, $CO_2H$, alkoxycarbonyl having 1, 2, 3, 4, 5 or 6 carbon atoms, alkylcarbonyl having 1, 2, 3, 4, 5 or 6 carbon atoms, $CONH_2$, CONRaRb, alkylsulfonylamino with alkyl having 1, 2, 3, 4, 5 or 6 carbon atoms, cyano, polyfluoroalkyl having 1, 2, 3 or 4 carbon atoms, polyfluoroalkoxy having 1, 2 or 3 carbon atoms and $SO_3H$, preferably alkyl having 1, 2, 3, 4, 5 or 6 carbon atoms, NRaRb, hydroxyl and $S(O)_n R_3$, more preferably methyl, $N(CH_3)_2$, hydroxyl and $SO_2CH_3$.

In another embodiment of this invention, the compounds of formula I are defined as above and n is 2.

In another embodiment of this invention, the compounds of formula I are defined as above and R3 represents alkyl having 1, 2, 3, 4, 5 or 6 carbon atoms, preferably methyl or ethyl, more preferably methyl.

In another embodiment of this invention, the compounds of formula I are defined as above and Ra and Rb represent, independently of one another, alkyl having 1, 2, 3, 4, 5 or 6 carbon atoms, preferably one of Ra and Rb represents methyl or ethyl and more preferably methyl.

Specific preference is given to a compound of formula I, characterized in that it is selected from the group consisting of:

N-[1-quinolin-3-yl)-1H-pyrrolo[2,3-b]pyridine-3-carbonyl] guanidine,

N-[1-quinolin-5-yl)-1H-pyrrolo[2,3-b]pyridine-3-carbonyl] guanidine,

N-[1-quinolin-6-yl)-1H-pyrrolo[2,3-b]pyridine-3-carbonyl] guanidine,

N-[1-quinolin-7-yl)-1H-pyrrolo[2,3-b]pyridine-3-carbonyl] guanidine,

N-[1quinolin-8-yl)-1H-pyrrolo[2,3-b]pyridine-3-carbonyl] guanidine,

N-[1-(isoquinoiin-5-yl)-1H-pyrrolo[2,3-b]pyridine-3-carbonyl]guanidine,

N-[1-(cinnolin-4-yl)-1H-pyrrolo[2,3-b]pyridine-3-carbonyl]guanidine,

N-[1-(quinazolin-4-yl)-1H-pyrrolo[2,3-b]pyridine-3-carbonyl]guanidine,

N-[1-(quinazolin-7-yl)-1H-pyrrolo[2,3-b]pyridine-3-carbonyl]guanidine,

N-[1-(2-methylquinazolin-4-yl)-1H-pyrrolo[2,3-b]pyridine-3-carbonyl]guanidine,

N-[1-(1,5-naphthyridin-4-yl)-1H-pyrrolo[2,3-b]pyridine-3-carbonyl]guanidine,

N-[1-(1,6-naphthyridin-4-yl)-1H-pyrrolo[2,3-b]pyridine-3-carbonyl]guanidine,

N-[1-(1,7-naphthyridin-4-yl)-1H-pyrrolo[2,3-b]pyridine-3-carbonyl]guanidine,

N-[1-(1,8-naphthyridin-4-yl)-1H-pyrrolo[2,3-b]pyridine-3-carbonyl]guanidine,

N-[1-(2-amino-1,8-naphthyridin-4-yl)-1H-pyrrolo[2,3-b] pyridine-3-carbonyl]guanidine, N-[1-(quinoxalin-5-yl)-1H-pyrrolo[2,3-b]pyridine-3-carbonyl]guanidine, N-[1-(pyridin-3-yl)-1H-pyrrolo[2,3-b]pyridine-3-carbonyl] guanidine, N-[1-(pyrimidin-2-yl)-1H-pyrrolo[2,3-b]pyridine-3-carbonyl]guanidine, N-[1-(pyrimidin-4-yl)-1H-pyrrolo[2,3-b]pyridine-3-carbonyl]guanidine, N-[1-(pyrimidin-5-yl)-1H-pyrrolo[2,3-b]pyridine-3-carbonyl]guanidine,
N-[1-(pyrazin-2-yl)-1H-pyrrolo[2,3-b]pyridine-3-carbonyl]guanidine,
N-[1-(benzothiazol-4-yl)-1H-pyrrolo[2,3-b]pyridine-3-carbonyl]guanidine,
N-[1-(benzimidazol-4-yl)-1H-pyrrolo[2,3-b]pyridine-3-carbonyl]guanidine,
N-[1-(indol-4-yl)-1H-pyrrolo[2,3-b]pyridine-3-carbonyl]guanidine,
N-[1-(indol-5-yl)-1H-pyrrolo[2,3-b]pyridine-3-carbonyl]guanidine,
N-[1-(1-(methylsulfonyl)indol-4-yl)-1H-pyrrolo[2,3-b]pyridine-3-carbonyl]guanidine,
N-[1-(7-azaindol-4-yl)-1H-pyrrolo[2,3-b]pyridine-3-carbonyl]guanidine,
N-[1-(pyrrolo[2,3-d]pyrimidin-4-yl)-1H-pyrrolo[2,3-b]pyridine-3-carbonyl]guanidine,
N-[1-(7-methylpyrrolo[2,3-d]pyrimidin-4-yl)-1H-pyrrolo[2,3-b]pyridine-3-carbonyl]guanidine,
N-[1-(thiazol-2-yl)-1H-pyrrolo[2,3-b]pyridine-3-carbonyl]guanidine,
N-[1-(imidazol-2-yl)-1H-pyrrolo[2,3-b]pyridine-3-carbonyl]guanidine,
N-[1-(imidazol-4-yl)-1H-pyrrolo[2,3-b]pyridine-3-carbonyl]guanidine,
N-[1-(3-(methylsulfonyl)phenyl)-1H-pyrrolo[2,3-b]pyridine-3-carbonyl]guanidine,
N-[1-(2-(methylsulfonyl)phenyl)-1H-pyrrolo[2,3-b]pyridine-3-carbonyl]guanidine,
N-[1-(2-hydroxyquinolin-4-yl)-1H-pyrrolo[2,3-b]pyridine-3-carbonyl]guanidine,
N-[1-(2-methylquinolin-4-yl)-1H-pyrrolo[2,3-b]pyridine-3-carbonyl]guanidine,
N-[1-(quinolin-4-yl)-1H-pyrrolo[2,3-b]pyridine-3-carbonyl]guanidine,
N-[1-(quinolin-2-yl)-1H-pyrrolo[2,3-b]pyridine-3-carbonyl]guanidine,
N-[1-(isoquinolin-1-yl)-1H-pyrrolo[2,3-b]pyridine-3-carbonyl]guanidine,
N-[1-(pyridin-2-yl)-1H-pyrrolo[2,3-b]pyridine-3-carbonyl]guanidine,
N-[1-(pyridin-4-yl)-1H-pyrrolo[2,3-b]pyridine-3-carbonyl]guanidine,
N-[1-(4-(methylsulfonyl)phenyl)-1H-pyrrolo[2,3-b]pyridine-3-carbonyl]guanidine,
N-[1-(3-(dimethylamino)phenyl)-1H-pyrrolo[2,3-b]pyridine-3-carbonyl]guanidine,
N-[1-(7-methyl-7H-pyrrolo[2,3-d]pyrimidin-4-yl)-1H-pyrrolo[2,3-b]pyridine-3-carbonyl]-guanidine, and
N-[1-(2-hydroxy-quinolin-4-yl)-1H-pyrrolo[2,3-b]pyridine-3-carbonyl]-guanidine and racemates, enantiomers and diastereomers and mixtures thereof, tautomers thereof and pharmaceutically acceptable salts thereof.

More specific preference is given to a compound of the formula I, characterized in that it is selected from the group consisting of:
N-[1-(2-hydroxyquinolin-4-yl)-1H-pyrrolo[2,3-b]pyridine-3-carbonyl]guanidine,
N-[1-(2-methylquinolin-4-yl)-1H-pyrrolo[2,3-b]pyridine-3-carbonyl]guanidine,
N-[1-(quinolin-4-yl)-1H-pyrrolo[2,3-b]pyridine-3-carbonyl]guanidine,
N-[1-(quinolin-2-yl)-1H-pyrrolo[2,3-b]pyridine-3-carbonyl]guanidine,
N-[1-(isoquinolin-1-yl)-1H-pyrrolo[2,3-b]pyridine-3-carbonyl]guanidine,
N-[1-(pyridin-2-yl)-1H-pyrrolo[2,3-b]pyridine-3-carbonyl]guanidine,
N-[1-(pyridin-4-yl)-1H-pyrrolo[2,3-b]pyridine-3-carbonyl]guanidine,
N-[1-(4-(methylsulfonyl)phenyl)-1H-pyrrolo[2,3-b]pyridine-3-carbonyl]guanidine,
N-[1-(3-(dimethylamino)phenyl)-1H-pyrrolo[2,3-b]pyridine-3-carbonyl]guanidine,
N-[1-(7-methyl-7H-pyrrolo[2,3-d]pyrimidin-4-yl)-1H-pyrrolo[2,3-b]pyridine-3-carbonyl]-guanidine, and
N-[1-(2-hydroxy-quinolin-4-yl)-1H-pyrrolo[2,3-b]pyridine-3-carbonyl]-guanidine and racemates, enantiomers and diastereomers and mixtures thereof, tautomers thereof and pharmaceutically acceptable salts thereof.

DETAILED DESCRIPTION OF THE INVENTION

If the compounds of this invention contain one or more centers of asymmetry, these may independently of one another have the S and the R configuration. The compounds may be in the form of isomers, diastereomers, racemates or mixtures thereof in any ratio.

The present invention encompasses all tautomeric forms of the compounds of formula I.

Alkyl radicals may be straight-chain or branched. This also applies if they carry substituents or occur as substituents of other radicals, for example in alkylamino, alkylcarbonylamino, alkoxy, alkoxycarbonyl, alkylcarbonyl, polyfluoroalkyl or polyfluoroalkoxy radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl) pentyl or hexyl. Preferred alkyl radicals are methyl, ethyl, n-propyl, isopropyl, tert-butyl and isobutyl. One or more, for example 1, 2, 3, 4, 5, 6, 7, 8 or 9, hydrogen atoms in alkyl radicals may be replaced by fluorine atoms to form polyfluoroalkyl radicals with alkyl having 1, 2, 3 or 4 carbon atoms. Examples of such radicals are difluoromethyl, trifluoromethyl, pentafluoroethyl, 2,2,2-trifluoroethyl, 3,3,3-trifluoropropyl and 4,4,4-trifluorbutyl. Polyfluoroalkoxy radicals are alkoxy radicals of 1 to 3 carbons substituted by 1, 2, 3, 4, 5, 6 or 7 fluorine atoms, in particular trifluoromethoxy. Alkoxy radicals comprise 1, 2, 3, 4, 5 or 6 carbon atoms and may be straight-chain or branched; a preferred alkoxy radical is methoxy.

Examples of cycloalkyl radicals are cyclopropyl, cyclobutyl, cyclopentyl, cyclohexyl or cycloheptyl. Substituted cycloalkyl radicals may be substituted in any positions.

The aryl radicals are chosen from phenyl, naphthyl and indenyl. The aryl radicals may be attached at any position. Substituted aryl radicals may be substituted at any position by one or more, for example by one, two or three, identical or different substituents selected from the group consisting of alkyl having 1, 2, 3, 4, 5 or 6 carbon atoms, cycloalkyl having 3, 4, 5, 6 or 7 carbon atoms, F, Cl, Br, I, $NO_2$, $NH_2$, alkylamino with alkyl having 1, 2, 3, 4, 5 or 6 carbon atoms, NRaRb, alkylcarbonylamino having 1, 2, 3, 4, 5 or 6 carbon atoms, hydroxyl, alkoxy having 1, 2, 3, 4, 5 or 6 carbon atoms, $S(O)_nR_3$, $CO_2H$, alkoxycarbonyl having 1, 2, 3, 4, 5 or 6 carbon atoms, alkylcarbonyl having 1, 2, 3, 4, 5 or 6 carbon atoms, $CONH_2$, CONRaRb, alkylsulfonylamino with alkyl having 1, 2, 3, 4, 5 or 6 carbon atoms, cyano, polyfluoroalkyl having 1, 2, 3 or 4 carbon atoms, polyfluoroalkoxy having 1, 2 or 3 carbon atoms and $SO_3H$, preferably by substituents selected from the group consisting of alkyl having 1, 2, 3, 4, 5 or 6 carbon atoms, NH₂, NRaRb, hydroxyl and SO₂R₃, more preferably by methyl, NH₂, N(methyl)₂, hydroxy and SO₂CH₃, especially preferably by N(methyl)₂ and SO₂CH₃ Preferably the aryl radicals are substituted by one substituent.

Heteroaryl radicals are monocyclic or bicyclic aromatic 3, 4, 5, 6, 7, 8, 9 or 10-membered ring compounds in which 1, 2, 3 or 4 ring atoms are oxygen atoms, sulfur atoms or nitrogen atoms, e.g. 1, 2 or 3 nitrogen atoms, 1 or 2 oxygen atoms, 1 or 2 sulfur atoms or a combination of various heteroatoms. The heteroaryl radicals may be attached at any position, for example at the 1 position, 2 position, 3 position, 4 position, 5 position, 6 position, 7 position or 8 position. Examples of heteroaryl are pyrimidinyl, thiazolyl, thienyl, pyrrolyl, pyridinyl, furyl, imidazolyl, oxazolyl, pyrazinyl, tetrazolyl, pyrazolyl, azaindolyl, quinolinyl, isoquinolinyl, cinnolinyl, quinazolinyl, naphthyridinyl, quinoxalinyl, benzothiazoleyl, benzimidazolyl, indolyl, 7-azaindolyl pyrrolo [2,3-d]pyrimidinyl, triazolyl, isoxazolyl, isothiazolyl, indazolyl and phthalazinyl, in particular pyrimidinyl, thiazolyl, thienyl, pyrrolyl, pyridinyl, furyl, imidazolyl, oxazolyl, pyrazinyl, tetrazolyl, pyrazolyl, azaindolyl, quinolinyl, isoquinolinyl, cinnolinyl, quinazolinyl, naphthyridinyl, quinoxalinyl, benzothiazolyl, benzimidazolyl, indolyl, 7-azaindolyl pyrrolo[2,3-d]pyrimidinyl; preferred are pyridinyl, pyrimidinyl, pyrazinyl, thiazolyl, imidazolyl, quinolinyl, isoquinolinyl, cinnolinyl, quinazolinyl, naphthyridinyl, quinoxalinyl, benzothiazolyl, benzimidazolyl, indolyl, 7-azaindolyl and pyrrolo[2,3-d]pyrimidinyl. Substituted heteroaryl radicals may be substituted in any positions by one or more, for example by one, two or three, substituents selected from the group consisting of alkyl having 1, 2, 3, 4, 5 or 6 carbon atoms, cycloalkyl having 3, 4, 5, 6 or 7 carbon atoms, F, Cl, Br, I, NO₂, NH₂, alkylamino with alkyl having 1, 2, 3, 4, 5 or 6 carbon atoms, NRaRb, alkylcarbonylamino having 1, 2, 3, 4, 5 or 6 carbon atoms, hydroxyl, alkoxy having 1, 2, 3, 4, 5 or 6-carbon atoms, $S(O)_nR_3$, CO₂H, alkoxycarbonyl having 1, 2, 3, 4, 5 or 6 carbon atoms, alkylcarbonyl having 1, 2, 3, 4, 5 or 6 carbon atoms, CONH₂, CONRaRb, alkylsulfonylamino with alkyl having 1, 2, 3, 4, 5 or 6 carbon atoms, cyano, polyfluoroalkyl having 1, 2, 3 or 4 carbon atoms, polyfluoroalkoxy having 1, 2 or 3 carbon atoms and SO₃H, preferably by substituents selected from the group consisting of alkyl having 1, 2, 3, 4, 5 or 6 carbon atoms, NH₂, NRaRb, hydroxyl and SO₂R₃, more preferably by methyl, NH₂, N(methyl)₂, hydroxy and SO₂CH₃, especially preferably methyl, NH₂, hydroxy and SO₂CH₃. Preferably the heteroaryl radicals are unsubstituted or substituted by one substituent.

If groups or substituents can occur several times in the compounds of formula I such as, for example R₂, Ra, Rb, aryl, heteroaryl, alkyl etc. they can all independently of one another have the meanings indicated and can in each case be identical or different.

The present invention furthermore encompasses derivatives of the compound of formula I, for example solvates, such as hydrates and adducts with alcohols, esters, prodrugs and other physiologically tolerated derivatives of compounds of formula I, and also active metabolites of compounds of formula I, for example N-[1-(2-hydroxy-quinolin-4-yl)-1H-pyrrolo[2,3-b]pyridine-3-carbonyl]-guanidine:

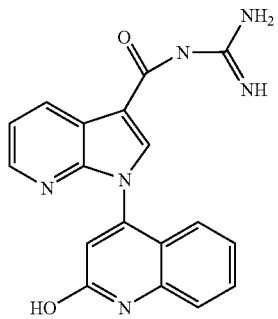

The compounds of formula I inhibit the cellular sodium-proton antiporter (Na⁺/H⁺ exchanger, NHE); in particular they inhibit the subtype NHE1. Because of the NHE-inhibitory properties, the compounds of formula I and/or the pharmaceutically acceptable salts thereof are suitable for the prevention and treatment of diseases caused by activation of or activated NHE, and of diseases caused secondarily by the NHE-related damage.

The compounds of formula (I) can be used as novel medicaments in the treatment of diseases as inhibitors of NHE and in particular of NHE-1 with good selectivity for NHE-1 with respect to NHE-2. This good selectivity makes it possible to reduce the potential gastrointestinal side effects existing with regard to molecules having inadequate selectivity (J. Clin. Invest., 1998, 101(6), 1243; Comparative Medicine, 2000, 50(5), 511).

Since NHE inhibitors predominantly act via their effect on cellular pH regulation, they can generally be combined beneficially with other compounds which regulate the intracellular pH, with suitable combination partners being, for example, inhibitors of the carbonate dehydratase enzyme group, inhibitors of systems transporting bicarbonate ions, such as of the sodium bicarbonate cotransporter (NBC) or of the sodium-dependent chloride-bicarbonate exchanger (NCBE), and NHE inhibitors with inhibitory effect on other NHE subtypes, because it is possible through them to enhance or modulate the pharmacologically relevant pH-regulating effects of the NHE inhibitors described herein.

The use of the compounds of the invention relates to the prevention and treatment of acute and chronic diseases in veterinary and human medicine, in particular human medicine.

Thus, the NHE inhibitors of the invention are suitable for the treatment of diseases caused by ischemia and by reperfusion.

The compounds described herein are suitable as antiarrhythmic medicaments.

Owing to their cardioprotective component, the NHE inhibitors of the formula I and/or the pharmaceutically acceptable salts thereof are outstandingly suitable for infarction prophylaxis and infarction treatment and for the treatment of angina pectoris, in which cases they also preventively inhibit or greatly reduce the pathophysiological processes associated with the development of ischemia-induced damage, in particular in the triggering of ischemia-induced cardiac arrhythmias. Because of their protective effects against pathological hypoxic and ischemic situations, the compounds of formula I and/or the pharmaceutically acceptable salts thereof used according to the invention can, because of inhibition of the cellular Na⁺/H⁺ exchange mechanism, be used as medicaments for the treatment of all acute or chronic ischemia-induced damage or diseases induced primarily or secondarily thereby.

This also relates to their use as medicaments for surgical interventions. Thus, the compounds can be used during organ transplantations, it being possible to use the compounds both to protect the organs in the donor before and during the removal, to protect removed organs for example during treatment with or storage thereof in physiological bath liquids, and during transfer to the recipient organism.

The compounds of the invention are likewise valuable medicaments with a protective effect when performing angioplastic surgical interventions, for example on the heart as well as on peripheral organs and vessels.

It has emerged that NHE inhibitors are exceptionally effective medicaments for the treatment of life-threatening arrhythmias. Ventricular fibrillation is terminated and the physiological sinus rhythm of the heart is restored.

Since NHE1 inhibitors of human tissue and organs, especially the heart, protect effectively not only against damage caused by ischemia and reperfusion but also against the cytotoxic effect of medicaments like those used in particular in cancer therapy and the therapy of autoimmune diseases, combined administration with the compounds of formula I and/or the pharmaceutically acceptable salts thereof is suitable for inhibiting the cytotoxic, especially cardiotoxic, side effects of said compounds. The reduction in the cytotoxic effects, especially the cardiotoxicity, resulting from comedication with NHE1 inhibitors makes it additionally possible to increase the dose of the cytotoxic therapeutic agents and/or to prolong the medication with such medicaments. The therapeutic benefits of such a cytotoxic therapy can be considerably increased by combination with NHE inhibitors.

In addition, the NHE1 inhibitors of the invention of formula I and/or the pharmaceutically acceptable salts thereof can be used when there is heart-damaging overproduction of thyroid hormones, thyrotoxicosis, or on external supply of thyroid hormones. The compounds of formula I and/or the pharmaceutically acceptable salts thereof are thus suitable for improving therapy with cardiotoxic medicaments.

In accordance with their protective effect against ischemia-induced damage, the compounds of the invention are also suitable as medicaments for the treatment of ischemias of the nervous system, especially of the central nervous system, being suitable for example for the treatment of stroke or of cerebral edema.

The compounds of formula I and/or the pharmaceutically acceptable salts thereof are also suitable for the therapy and prophylaxis of diseases and disorders induced by overexcitability of the central nervous system, in particular for the treatment of epileptic disorders, centrally induced clonic and tonic spasms, states of psychological depression, anxiety disorders and psychoses. In these cases it is possible to use the NHE inhibitors described herein alone or in combination with other substances with antiepileptic activity or antipsychotic active ingredients, or carbonate dehydratase inhibitors, for example with acetazolamide, and with other inhibitors of NHE or of the sodium-dependent chloride-bicarbonate exchanger (NCBE).

The compounds according to the invention of formula I and/or the pharmaceutically acceptable salts thereof are additionally likewise suitable for the treatment of types of shock such as, for example, of allergic, cardiogenic, hypovolemic and bacterial shock.

The compounds of formula I and/or the pharmaceutically acceptable salts thereof can likewise be used for the prevention and treatment of thrombotic disorders because they, as NHE inhibitors, are able to inhibit platelet aggregation themselves. They are additionally able to inhibit or prevent the excessive release, occurring after ischemia and reperfusion, of mediators of inflammation and coagulation, especially of von Willebrand factor and of thrombogenic selectin proteins. It is thus possible to reduce and eliminate the pathogenic effect of significant thrombogenic factors. The NHE inhibitors of the present invention can therefore be combined with other anticoagulant and/or thrombolytic active ingredients such as, for example, recombinant or natural tissue plasminogen activator, streptokinase, urokinase, acetylsalicylic acid, thrombin antagonists, factor Xa antagonists, medicinal substances with fibrinolytic activity, thromboxane receptor antagonists, phosphodiesterase inhibitors, factor VIIa antagonists, clopidogrel, ticlopidine etc. Combined use of the present NHE inhibitors with NCBE inhibitors and/or with inhibitors of carbonate dehydratase such as, for example, with acetazolamide, is particularly beneficial.

The compounds of formula I and/or the pharmaceutically acceptable salts thereof used according to the invention are additionally distinguished by a strong inhibitory effect on the proliferation of cells, for example fibroblast proliferation and the proliferation of smooth vascular muscle cells. The compounds of formula I and/or the pharmaceutically acceptable salts thereof are therefore suitable as valuable therapeutic agents for diseases in which cellular proliferation represents a primary or secondary cause, and can therefore be used as antiatherosclerotics, agents for chronic renal failure, cancers.

It was possible to show that cell migration is inhibited by NHE inhibitors. The compounds of formula I and/or the pharmaceutically acceptable salts thereof are therefore suitable as valuable therapeutic agents for diseases in which cell migration represents a primary or secondary cause, such as, for example, cancers with a pronounced tendency to metastasis.

The compounds of formula I and/or the pharmaceutically acceptable salts thereof are further distinguished by a retardation or prevention of fibrotic disorders. They are thus suitable as excellent agents for the treatment of cardiac fibroses, and of pulmonary fibrosis, hepatic fibrosis, renal fibrosis and other fibrotic disorders.

They can thus be used for the treatment of organ hypertrophies and hyperplasias, for example of the heart and the prostate. They are therefore suitable for the prevention and treatment of heart failure (congestive heart failure=CHF) and for the treatment and prevention of prostate hyperplasia or prostate hypertrophy.

Since there is significant elevation in NHE in essential hypertensives, the compounds of formula I and/or the pharmaceutically acceptable salts thereof are suitable for the prevention and treatment of high blood pressure and of cardiovascular disorders. In these cases they can be used alone or with a suitable combination and formulation partner for the treatment of high blood pressure and of cardiovascular disorders. Thus, for example, they can be combined with one or more diuretics with a thiazide-like action, loop diuretics, aldosterone and pseudoaldosterone antagonists, such as hydrochlorothiazide, indapamide, polythiazide, furosemide, piretamide, torasemide, bumetamide, amiloride, triamterene, spironolactone or eplerone. The NHE inhibitors of the present invention can further be used in combination with calcium channel blockers such as verapamil, diltiazem, amlodipine or nifedipine, and with ACE inhibitors such as, for example, ramipril, enalapril, lisinopril, fosinopril or captopril. Further beneficial combination partners are also beta-blockers such as metoprolol, albuterol etc., antagonists of the angiotensin receptor and its receptor subtypes such as losartan, irbesartan, valsartan; omapatrilat, gemopatrilat, endothelin antagonists, renin inhibitors, adenosine receptor agonists, inhibitors and activators of potassium channels such as glibenclamide, glimepiride, diazoxide, cromakalim, minoxidil and derivatives thereof, activators of the mitochondrial ATP-sensitive potassium channel (mitoK(ATP) channel), inhibitors of Kv1.5 etc.

It has emerged that NHE1 inhibitors of formula I and/or the pharmaceutically acceptable salts thereof have a significant antiinflammatory effect and can thus be used as antiinflammatory drugs. Inhibition of the release of mediators of inflammation is noteworthy in this connection. The compounds can thus be used alone or in combination with an antiinflammatory drug for the prevention or treatment of chronic and acute inflammatory disorders. Combination partners advantageously used are steroidal and non-steroidal antiinflammatory drugs. The compounds of the invention can also be used for the treatment of disorders caused by protozoa, of malaria and of coccidiosis in poultry.

It has additionally been found that compounds of formula I and/or the pharmaceutically acceptable salts thereof show a beneficial effect on serum lipoproteins. It is generally acknowledged that blood fat levels which are too high, called hyperlipoproteinemias, represent an essential risk factor for the development of arteriosclerotic vascular lesions, especially coronary heart disease. The reduction of elevated serum lipoproteins therefore has exceptional importance for the prophylaxis and regression of atherosclerotic lesions. Besides the reduction in total serum cholesterol, it is particularly important to reduce the proportion of specific atherogenic lipid fractions of this total cholesterol, in particular of the low density lipoproteins (LDL) and of the very low density lipoproteins (VLDL), because these lipid fractions represent an atherogenic risk factor. By contrast, a protective function against coronary heart disease is ascribed to the high density lipoproteins. Accordingly, hypolipidemics should be able to reduce not only total cholesterol but, in particular, the VLDL and LDL serum cholesterol fractions. It has been found that NHE1 inhibitors show valuable therapeutically utilizable properties in relation to influencing the serum lipid levels. Thus, they significantly reduce the elevated serum concentrations of LDL and VLDL as are to be observed, for example, due to increased dietary intake of a cholesterol- and lipid-rich diet or in cases of pathological metabolic alterations, for example genetically related hyperlipidemias. They can therefore be used for the prophylaxis and regression of atherosclerotic lesions by eliminating a causal risk factor. Included herein are not only the primary hyperlipidemias but also certain secondary hyperlipidemias occurring, for example, in association with diabetes. In addition, the compounds of formula I and/or the pharmaceutically acceptable salts thereof lead to a marked reduction in the infarctions induced by metabolic abnormalities and, in particular, to a significant reduction in the induced infarct size and the severity thereof. Said compounds are therefore advantageously used for producing a medicament for the treatment of hypercholesterolemia; for producing a medicament for the prevention of atherogenesis; for producing a medicament for the prevention and treatment of atherosclerosis, for producing a medicament for the prevention and treatment of diseases induced by elevated cholesterol levels, for producing a medicament for the prevention and treatment of diseases induced by endothelial dysfunction, for producing a medicament for the prevention and treatment of atherosclerosis-induced hypertension, for producing a medicament for the prevention and treatment of atherosclerosis-induced thromboses, for producing a medicament for the prevention and treatment of hypercholesterolemia-induced and endothelial dysfunction-induced ischemic damage and post-ischemic reperfusion damage, for producing a medicament for the prevention and treatment of hypercholesterolemia-induced and endothelial dysfunction-induced cardiac hypertrophies and cardiomyopathies and of congestive heart failure (CHF), for producing a medicament for the prevention and treatment of hypercholesterolemia-induced and endothelial dysfunction-induced coronary vasospasms and myocardial infarctions, for producing a medicament for the treatment of said disorders in combinations with hypotensive substances, preferably with angiotensin converting enzyme (ACE) inhibitors and angiotensin receptor antagonists. A combination of an NHE inhibitor of formula I and/or the pharmaceutically acceptable salts thereof with an active ingredient lowering the blood fat levels, preferably with an HMG-CoA reductase inhibitor (for example lovastatin or pravastatin), the latter bringing about a hypolipidemic effect and thus increasing the hypolipidemic properties of the NHE inhibitor of formula I and/or the pharmaceutically acceptable salts thereof, proves to be a favorable combination with enhanced effect and reduced use of active ingredients.

Thus, compounds of formula I and/or the pharmaceutically acceptable salts thereof lead to effective protection against endothelial damage of various origins. This protection of the vessels against the syndrome of endothelial dysfunction means that the compounds of formula I and/or the pharmaceutically acceptable salts thereof are valuable medicaments for the prevention and treatment of coronary vasospasms, peripheral vascular diseases, in particular intermittent claudication, atherogenesis and atherosclerosis, left ventricular hypertrophy and dilated cardiomyopathy and thrombotic disorders.

It has additionally been found that compounds of formula I and/or the pharmaceutically acceptable salts thereof are suitable in the treatment of non-insulin-dependent diabetes (NIDDM), with the insulin resistance being restrained. It may in this connection be beneficial, to enhance the antidiabetic activity and quality of the effect of the compounds of the invention, to combine them with a biguanide such as metformin, with an antidiabetic sulfonylurea such as glyburide, glimepiride, tolbutamide etc., with a glucosidase inhibitor, with a PPAR agonist such as rosiglitazone, pioglitazone etc., with an insulin product of different administration form, with a DB4 inhibitor, with an insulin sensitizer or with meglitinide.

Besides the acute antidiabetic effects, the compounds of formula I and/or the pharmaceutically acceptable salts thereof counteract the development of late complications of diabetes and can therefore be used as medicaments for the prevention and treatment of late damage from diabetes, such as diabetic nephropathy, diabetic retinopathy, diabetic cardiomyopathy and other disorders occurring as a consequence of diabetes. They can in this connection be advantageously combined with the antidiabetic medicaments just described under NIDDM treatment. The combination with a beneficial dosage form of insulin should be particularly important in this connection.

The NHE inhibitors of the invention of formula I and/or the pharmaceutically acceptable salts thereof show, besides the protective effects against acute ischemic events and the subsequent equally acutely stressing reperfusion events, also direct therapeutically utilizable effects against diseases and disorders of the entire mammalian organism which are associated with the manifestations of the chronically progressive aging process and which occur independently of acute hypoperfusion states and under normal, non-ischemic conditions. These pathological, age-related manifestations induced over the long aging period, such as illness, invalidity and death, which can now be made amenable to treatment with NHE inhibitors, are diseases and disorders which are essentially caused by age-related changes in vital organs and the function thereof and become increasingly important in the aging organism.

Disorders connected with an age-related functional impairment or with age-related manifestations of wear of organs are, for example, the inadequate response and reactivity of the blood vessels to contraction and relaxation reactions. This age-related decline in the reactivity of vessels to constricting and relaxing stimuli, which are an essential process of the cardiovascular system and thus of life and health, can be significantly eliminated or reduced by NHE inhibitors. One important function and a measure of the maintenance of the reactivity of vessels is the blockade or retardation of the age-related progression in endothelial dysfunction, which can be eliminated in a highly significant manner by NHE inhibitors. The compounds of formula I and/or the pharmaceutically acceptable salts thereof are thus outstandingly suitable for the treatment and prevention of the age-related progression in endothelial dysfunction, especially of intermittent claudication.

An example of another variable characterizing the aging process is the decline in the contractability of the heart and the decline in the adaptation of the heart to a required pumping output of the heart. This diminished efficiency of the heart as a consequence of the aging process is in most cases connected with a dysfunction of the heart which is caused inter alia by deposition of connective tissue in the myocardial tissue. This deposition of connective tissue is characterized by an increase in the weight of the heart, by an enlargement of the heart and by restrictive cardiac function. It was surprising that it was possible almost completely to inhibit such aging of the heart organ. The compounds of formula I and/or the pharmaceutically acceptable salts thereof are thus outstandingly suitable for the treatment and prevention of heart failure, of congestive heart failure (CHF).

Whereas preceding patents and patent applications have claimed the treatment of various forms of cancer which have already occurred, it was extremely surprising that not only is it possible to cure a cancer which has already occurred through inhibition of proliferation, but there is also prevention and highly significant retardation of the age-related incidence of cancer by NHE inhibitors. A particularly noteworthy finding is that the disorders, occurring as a result of aging, of all organs and not only certain types of cancer are suppressed or occur with a highly significant delay. The compounds of formula I and/or the pharmaceutically acceptable salts thereof are thus outstandingly suitable for the treatment and, in particular, the prevention of age-related types of cancer.

There is found to be not only a delay, shifted highly significantly in time and beyond the normal statistical extent, in the occurrence of age-related disorders of all the organs investigated, including the heart, vessels, liver etc., and a highly significant delay in cancer of the elderly. On the contrary, there is also surprisingly a prolongation of life to an extent which has to date been achievable by no other group of medicaments or by any natural products. This unique effect of NHE inhibitors also makes it possible, besides the use of the active ingredients alone on humans and animals, to combine these NHE inhibitors with other active principles, measures, substances and natural products which are used in gerontology and which are based on a different mechanism of action. Such classes of active ingredients used in gerontological therapy are: in particular vitamins and substances with antioxidant activity. Since there is a correlation between caloric load or food intake and the aging process, the combination with dietary measures can take place for example with appetite suppressants. It is likewise possible to consider a combination with hypotensive medicaments such as with ACE inhibitors, angiotensin receptor antagonists, diuretics, $Ca^{2+}$ antagonists etc. or with metabolism-normalizing medicaments such as cholesterol-lowering agents.

The compounds of formula I and/or the pharmaceutically acceptable salts thereof are thus outstandingly suitable for the prevention of age-related tissue changes and for prolonging life while retaining a high quality of life.

The compounds of the invention are effective inhibitors of the cellular sodium-proton antiporter (Na/H exchanger) which in a large number of disorders (essential hypertension, atherosclerosis, diabetes etc.) is also increased in cells which are readily amenable to measurements, such as, for example, in erythrocytes, platelets or leucocytes. The compounds according to the invention are therefore suitable as outstanding and simple scientific tools, for example in their use as diagnostic agents for determining and distinguishing different types of hypertension, but also of atherosclerosis, diabetes and the late complications of diabetes, proliferative disorders etc.

The present invention also relates to processes for the synthesis compounds of formula I and/or the pharmaceutically acceptable salts thereof.

The invention further relates to a process for preparing a compound of formula I and/or the pharmaceutically acceptable salts thereof, which comprises reacting a compound of the formula II

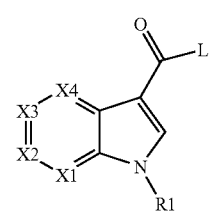

in which $X_1$, $X_2$, $X_3$, $X_4$ and R1 have the same meanings as in the formula I and L is a leaving group which can easily undergo nucleophilic displacement by guanidine.

L can be selected for example from the following group: hydroxy, chloride, bromide, alkoxy in which the alkyl radical is an optionally substituted alkyl group with 1, 2, 3, 4, 5 or 6 carbon atoms, phenoxy, phenylthio, methylthio, 2-pyridylthio group and a nitrogen heterocycle, for example 1-imidazolyl; preferably L is chloride or methoxy.

The compounds of formula I can be obtained from the compounds of formula II according to the following general synthetic scheme

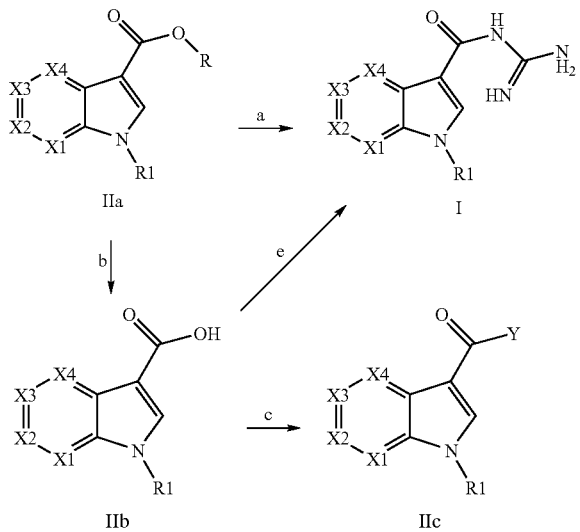

in which $X_1$, $X_2$, $X_3$, $X_4$ and R1 have the same meanings as in the formula I, Y is chloride or bromide, preferably chloride, and R is an optionally substituted alkyl group with 1, 2, 3, 4, 5 or 6 carbon atoms, preferably methyl.

Reaction a is generally carried out in the presence of guanidine hydrochloride and of a base, for example potassium tert-butoxide, in an inert solvent, such as dimethylformamide, at a temperature of between 20° C. and the boiling point of the reaction medium, or in the presence of guanidine in a solvent, such as a ($C_1$–$C_4$) alcohol, for example isopropanol, at a temperature of between 20° C. and the boiling point of the reaction medium.

Reaction b is generally carried out according to the usual methods which do not affect the remainder of the molecule, in particular by applications of the methods described by T. W. Greene and P. G. M. Wuts, Protective Groups in Organic Synthesis (2nd ed.), A. Wiley—Interscience Publication (1991), or by McOmie, Protective groups in Organic Chemistry, Plenum Press (1973), or by Bradford P. Mundy and Michael G. Ellerd, Name Reactions and Reagents in Organic Synthesis, A. Wiley—Interscience Publication (1988). For example, the saponification reaction b is carried out in a basic medium, for example in the presence of lithium hydroxide monohydrate or sodium hydroxide, in an inert solvent, such as a mixture of tetrahydrofuran and of water, at a temperature of between 20° C. and the boiling point of the reaction medium, preferably at the reflux temperature of the reaction medium. Alternatively, this reaction can be carried out in the presence of boron tribromide in an inert solvent, such as dichloromethane, at a temperature of between −78° C. and the boiling point of the reaction medium, preferably at 0° C.

Reaction c is generally carried out according to the usual methods which do not affect the remainder of the molecule, in particular by applications of the methods described by Bradford P. Mundy and Michael G. Ellerd, Name Reactions and Reagents in Organic Synthesis, A. Wiley—Interscience Publication (1988). For example, reaction (c) is preferably carried out under an inert atmosphere (for example, under nitrogen or under argon) in the presence of oxalyl chloride in an inert solvent, such as dichloromethane, at a temperature of between 20° C. and the boiling point of the reaction medium, preferably at a temperature in the region of 20° C., or in the presence of thionyl chloride in an inert solvent, such as chloroform, at a temperature of between 20° C. and the boiling point of the reaction medium, preferably at the reflux temperature of the reaction medium.

Reaction d is generally carried out in the presence of guanidine hydrochloride and of a base, such as potassium tert-butoxide or sodium methoxide, in an inert solvent, such as dimethylformamide, at a temperature of between 20° C. and the boiling point of the reaction medium, or else in the presence of guanidine in a solvent, such as 1,2-dimethoxyethane, tetrahydrofuran or a mixture of tetrahydrofuran and dichloromethane, at a temperature of between 20° C. and the boiling point of the reaction medium.

Reaction e can be carried out in the presence of guanidine and of an activating agent of the 1-hydroxybenzotriazole hydrate (HOBT)/1-ethyl-3-[3-(dimethylamino)propyl]carbodiimide hydrochloride (EDCl) type, for example, in the presence of a base (triethylamine or diisopropylethylamine, for example) in an inert solvent (dimethylformamide, for example) at a temperature of between 0° C. and the boiling point of the medium, or according to the well known coupling methods of peptide chemistry (M. Bodanszky et al. Principles of Peptide Synthesis, Springer-Verlag, New York, N.Y., 1984, 9–58) or the well known methods for the formation of an amide. Alternatively, this reaction can be carried out, by adaptation of the method described by M. Baumgarth et al. (Eur. J. Org., 2000, 2253), in the presence of N-(benzyloxycarbonyl)guanidine and of an activating agent of the 2-chloro-1-methylpyridinium iodide type, for example, in the presence of a base (diisopropylethylamine, for example) in an inert solvent (1-methyl-2-pyrrolidinone, for example) at a temperature of between 0° C. and the boiling point of the reaction medium, followed by a cleavage reaction on the benzyloxycarbonyl protective group in the presence of palladium-on-charcoal and of hydrogen or else of a hydrogen donor, such as cyclohexene, in an inert solvent (acetone, for example) at a temperature of between 20° C. and the boiling point of the reaction medium, or by application or adaptation of the deprotection methods described by T. W. Greene et al. in Protective Groups in Organic Synthesis, third edition, 1999, Wiley-Interscience.

The compounds of formulae IIa and IIb can be obtained from the compounds of formula III, in which $X_1$, $X_2$, $X_3$ and $X_4$ and R1 have the same meanings as in the formula I, R is an optionally substituted alkyl group with 1, 2, 3, 4, 5 or 6 carbon atoms according to the following general synthetic scheme:

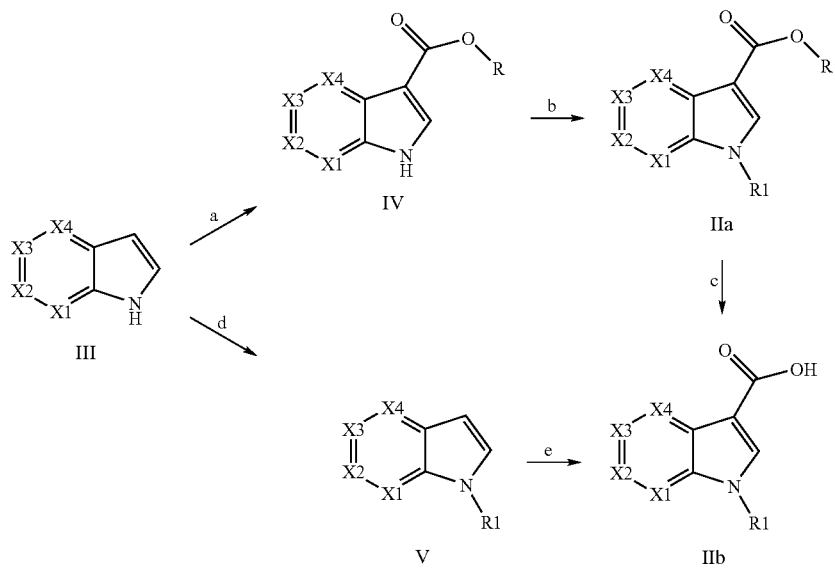

Reaction a can be carried out in the presence of trifluoroacetic anhydride, in an inert solvent, such as dimethylformamide, at a temperature of between 0° C. and the boiling point of the reaction medium, followed by a reaction in the presence of a hydride (preferably sodium hydride) and subsequently of water, in an inert solvent, such as dimethylformamide, at a temperature of between 20° C. and the boiling point of the reaction medium, followed, finally, by an esterification reaction, which can be carried out in the presence of sulfuric acid in an appropriate alcohol R—OH at a temperature of between 20° C. and the boiling point of the reaction medium or else according to the well known esterification methods (E. Haslam et al. Tetrahedron, 1980, 36, 2409).

Or reaction a can be carried out in the presence of hexamethylenetetramine, in a mixture of acetic acid and of water at a temperature of between 20° C. and the boiling point of the reaction medium, by adaptation of the method described by F. Buzzetti et al. (WO 96/16964), followed by an oxidation reaction, which can be carried out in the presence of sodium chlorite and of sodium phosphate in a mixture of 1,4-dioxane, of 2-methyl-2-butene and of water at a temperature of between 20° C. and the boiling point of the reaction medium or else according to the known methods for the oxidation of the aldehyde functional group to an acid functional group (R. C. Larock, Comprehensive Organic Transformations, VCH Publishers Inc. (1989), 838–841), followed, finally, by an esterification reaction, which can be carried out in the presence of sulfuric acid in the appropriate alcohol R—OH at a temperature of between 20° C. and the boiling point of the reaction medium or else according to the well known esterification methods (E. Haslam et al. Tetrahedron, 1980, 36, 2409).

Or reaction a can be carried out by application or adaptation of the method described by T. Wang et al. (J. Org. Chem., 2002, 67, 6226), followed by an oxidation reaction on the oxoacetate functional group by application or adaptation of the methods described by W. C. McDaniel et al. (WO 02/066416 A1) and by K. Kogure et al. (Agr. Biol. Chem., 1976, 40(2), 435), followed, finally, by an esterification reaction, which can be carried out in the presence of sulfuric acid in the appropriate alcohol R—OH at a temperature of between 20° C. and the boiling point of the reaction medium or else according to the well known esterification methods (E. Haslam et al. Tetrahedron, 1980, 36, 2409).

Reactions b and d can be carried out in the presence of an appropriate halide of formula R1-X where R1 has the same meaning as in formula I and X is fluorine, chlorine, bromine or iodine, preferably chlorine, bromine or iodine, preferably under an inert atmosphere (for example, under nitrogen or under argon) in a basic medium, either, for example, in the presence of sodium hydride and optionally of copper powder, in an inert solvent, such as dimethylformamide, at a temperature of between 20° C. and the boiling point of the reaction medium (preferably at a temperature in the region of 140° C.), or, for example, in the presence of potassium carbonate, in an inert solvent, such as dimethyl sulfoxide or dimethylformamide, at a temperature of between 20° C. and the boiling point of the reaction medium (preferably at a temperature in the region of 100° C.).

Alternatively, reactions b and d can be carried out, preferably under an inert atmosphere (for example, under nitrogen or under argon) in a basic medium, for example in the presence of potassium orthophosphate, of copper iodide and of trans-1,2-cyclohexanediamine or of N,N'-dimethylethylenediamine, in an inert solvent, such as a mixture of 1,4-dioxane and of n-dodecane or of toluene and of n-dodecane, at a temperature of between 20° C. and the boiling point of the reaction medium (preferably at a temperature in the region of 110° C.), by adaptation of the methods described by S. L. Buchwald et al. (J. Am. Chem. Soc., 2002, 124, 11684; 2001, 123, 7727).

Reaction c is generally carried out according to the usual methods which do not affect the remainder of the molecule, in particular by applications of the methods described by T. W. Greene and P. G. M. Wuts, Protective Groups in Organic Synthesis (2nd ed.), A. Wiley—Interscience Publication (1991), or by McOmie, Protective Groups in Organic Chemistry, Plenum Press (1973), or by Bradford P. Mundy and Michael G. Ellerd, Name Reactions and Reagents in Organic Synthesis, A. Wiley—Interscience Publication (1988). For example, the saponification reaction (c) is carried out in a basic medium, for example in the presence of lithium hydroxide monohydrate, in an inert solvent, such as a mixture of tetrahydrofuran and of water, at a temperature of between 20° C. and the boiling point of the reaction medium, preferably at the reflux temperature of the reaction medium.

Reaction e can be carried out in the presence of trifluoroacetic anhydride, in an inert solvent, such as dimethylformamide, at a temperature of between 0° C. and the boiling point of the reaction medium, followed by a reaction in the presence of a hydride (preferably sodium hydride) and subsequently of water, in an inert solvent, such as dimethylformamide, at a temperature of between 20° C. and the boiling point of the reaction medium.

Or reaction e can be carried out by application or adaptation of the method described by T. Wang et al. (J. Org. Chem., 2002, 67, 6226), followed by an oxidation reaction on the oxoacetate functional group by application or adaptation of the methods described by W. C. McDaniel et al. (WO 02/066416 A1) and by K. Kogure et al. (Agr. Biol. Chem., 1976, 40(2), 435).

The compounds of formula III can be obtained by application or adaptation of the methods described by T. Wang et al. (J. Org. Chem., 2002, 67, 6226), J. Parrick et al. (J. Chem. Soc., Perkin Trans. 1, 1976, 13, 1361), P. D. Cook (Synthesis and reactivity of pyrrolopyridazines, Diss. Abstr. Int. B, 1974, 35(3), 1199), H. Yamanaka et al. (Chem. Pharm. Bull., 1993, 41, 81), L. E. Crane (The synthesis and properties of adenine nucleosides, pyrrolo[3,2-d]pyrimidines and pyrrolo[2,3-d]pyrimidines, Diss. Abstr. Int. B, 1976, 37(5), 2242) and E. A. Meade (The synthesis and biological evaluation of pyrrolo[2,3-d]pyridazine and pyrrolo[2,3-d]pyridazine-7-one nucleosides, Diss. Abstr. Int. B, 1992, 52(10), 5282).

The halide compounds of formula R1 X where R1 has the same meaning as in the formula I and X is fluorine, chlorine, bromine or iodine, preferably chlorine, bromine or iodine, can be prepared by application or adaptation of the following methods: 2-haloquinolines can be obtained or application or adaptation of the methods described in Tetrahedron Lett., 2000, 41(15), 2663; Tetrahedron Lett., 1988, 29(48), 6287, and Synthesis, 1987, 11, 1013. 5-Haloquinolines, 6-haloquinolines, 7-haloquinolines and 8-haloquinolines can be obtained by application or adaptation of the methods described in patent DE 2322143 and in J. Chem. Soc., 1960, 561. 4-Haloquinolines can be obtained by application or adaptation of the methods described in J. Org. Chem., 1962, 27,1318. 5-Haloquinolines can be also be obtained by application or adaptation of the methods described in Synthesis, 2002, (1), 83. 1-Haloisoquinolines can be obtained by application or adaptation of the methods described in Tetrahedron Lett., 1988, 29(48), 6287; Journal of Chemical and Engineering Data, 1986, 31(4), 503; Synthesis, 1983, 10, 791, and J. Heterocyclic Chem., 1978, 15(8), 1513. 5-Haloisoquinolines can be obtained by application or adaptation of the methods described in Synthesis, 2002, (1), 83. 5-Haloquinoxalines can be obtained by application or adaptation of the methods described in J. Chem. Soc. Perkin Trans. 1, 1984, 3, 377, and in Synthesis, 2002, (1), 83. 4-Halo-1,8-naphthyridines can be obtained by application or adaptation of the methods described in Eur. J. Med. Chem., 1999, 34(6), 505, and in Synthesis, 1974, (11), 809. 4-Halo-1,5-naphthyridines can be obtained by application or adaptation of the methods described in patents WO 00/47576 and WO 99/58533 and in J. Org. Chem., 1971, 36(12), 1720. 4-Halo-1,6-naphthyridines can be obtained by application or adaptation of the methods described in patent WO 99/58533 and in Chemia, 1975, 18, 295. 4-Halo-1,7-naphthyridines can be obtained by application or adaptation of the methods described in J. Org. Chem., 1972, 37(20), 3101. 4-Haloquinazolines can be obtained by application or adaptation of the methods described in Journal of Environmental Sciences and Health, Part B, 1983, B18(4–5), 599. 7-Haloquinazolines can be obtained by application or adaptation of the methods described in Synthesis, 2002, (1), 83. 4-Halo-7-azaindoles can be obtained by application or adaptation of the methods described in patents WO 03/00690, WO 01/47922 and WO 01/46196 and in J. Chem. Soc. Perkin Trans. 1, 1974, 19, 513. 4-Haloindoles can be obtained by application or adaptation of the methods described in J. Org. Chem., 1983, 48(12), 2066. 4-Halocinnolines can be obtained by application or adaptation of the methods described in Braz. Pedido P I, 1978, 18. 4-Halobenzothiazoles can be obtained by application or adaptation of the methods described in J. Chem. Soc., section C, 1969, (2), 268. 2-Halopyrazines can be obtained by application or adaptation of the methods described in J. Org. Chem., 1959, 24, 345. 2-Haloimidazoles and 4-haloimidazoles can be obtained by application or adaptation of the methods described in J. Heterocyclic Chem., 1967, 4(3), 451. 4-Halopyrrolo[2,3-d]pyrimidines can be obtained by application or adaptation of the methods described in patent GB 915304 and in J. Chem. Soc., 1960, 131.

It is understood by a person skilled in the art that, for the implementation of the processes according to the invention which are described above, it may be necessary to introduce protective groups for the amine, carboxyl and alcohol functional groups in order to avoid side reactions. These groups are those which can be removed without affecting the remainder of the molecule. Mention may be made, as examples of protective groups for the amine functional group, of tert-butyl carbamate, which can be regenerated using iodotrimethylsilane or in an acidic medium (trifluoroacetic acid, or hydrochloric acid in a solvent, such as dioxane, for example), benzyl carbamate, which can be regenerated in the presence of hydrogen or in the presence of a mixture of a thiol (benzenethiol, for example) and of a Lewis acid (boron trifluoride etherate, for example), acetyl, which can be regenerated in an acidic medium (hydrochloric acid, for example), benzoyl, which can be regenerated in an acidic medium (hydrochloric acid, for example), or 2-(trimethylsilanyl)ethoxymethyl, which can be regenerated in the presence of tetrabutylammonium fluoride or in an acidic medium, for example (hydrochloric acid, for example). Mention may be made, as protective groups for the carboxyl functional group, of esters (methoxymethyl ester, benzyl ester or methyl ester, for example), which can be regenerated by the methods described by T. W. Greene et al. in Protective Groups in Organic Synthesis, third edition, 1999, Wiley-Interscience. Mention may be made, as protective groups for the alcohol functional group, of esters (benzoyl ester, for example), which can be regenerated in an acidic medium or by catalytic hydrogenation, or else of ethers, such as the methyl ether, for example, which can be regenerated in the presence of boron tribromide, or the benzyl ether, which can be regenerated by catalytic hydrogenation. Other protective groups which can be used are described by T. W. Greene et al. in Protective Groups in Organic Synthesis, third edition, 1999, Wiley-Interscience.

The general synthetic scheme for the preparation of the compounds of formula I is as follows, in which $X_1$, $X_2$, $X_3$ and $X_4$ and R1 have the same meanings as in the formula I, R is an optionally substituted alkyl group with 1, 2, 3, 4, 5 or 6 carbon atoms and X is fluorine, chlorine, bromine or iodine, a) reaction of a compound of formula III with an appropriate halide of formula R1-X to form a derivative of formula V,
b) introduction of a carboxylic acid functional group into the 3-position of the derivative of formula V, to form a derivative of formula IIb, or
a') introduction of a carboxylate functional group into the 3-position of the derivative of formula III, to form a derivative of formula IV,
b') reaction of a compound of formula IV with an appropriate halide of formula R1-X to form a derivative of formula IIa,
c') optional saponification of the derivative of formula IIa to the derivative of formula IIb,
d) reaction of the derivative of formula IIb with guanidine or protected guanidine and the optional deprotection of the product formed, or
d') reaction of the derivative of formula IIa with guanidine, or
c″) formation of the acid chloride IIc of the derivative of formula IIb,
d″) reaction of the acid chloride IIc with guanidine, the isolation of the product and its optional conversion to a pharmaceutically acceptable salt.

A preferred method for the preparation of the compounds of formula I, in which $X_1$, $X_2$, $X_3$ and $X_4$ and R1 have the same meanings as in the formula I, R is an optionally substituted alkyl group with 1, 2, 3, 4, 5 or 6 carbon atoms and X is fluorine, chlorine, bromine or iodine, comprises:
a) introduction of a carboxylate functional group into the 3-position of a derivative of formula III, to form a derivative of formula IV,
b) reaction of a compound of formula IV with an appropriate halide of formula R1-X to form a derivative of formula IIa,
c) saponification of the derivative of formula IIa to the derivative of formula IIb,
d) formation of the acid chloride IIc of the derivative of formula IIb,
e) reaction of the acid chloride IIc with guanidine, the isolation of the product and its optional conversion to a pharmaceutically acceptable salt.

The compounds of formula I can be isolated and purified by the usual known methods, for example by crystallization, chromatography or extraction.

The compounds of formula I can optionally be converted into addition salts with an inorganic or organic acid by reacting with such an acid in a solvent, e.g. an organic solvent such as an alcohol, a ketone, an ether or a chlorinated solvent. These salts also form part of the invention. Examples of pharmaceutically acceptable salts that can be mentioned include the following salts: benzenesulphonate, hydrobromide, hydrochloride, acetate, citrate, ethanesulphonate, fumarate, gluconate, iodate, maleate, isethionate, methanesulphonate, methylenebis(β-oxynaphthoate), nitrate, oxalate, pamoate, phosphate, salicylate, succinate, sulphate, tartrate, theophyllinacetate and p-toluenesulphonate. If the compounds contain an acid group, they are capable of forming salts with bases, for example alkali metal salts, preferably sodium or potassium salts, or ammonium salts, for example salts with ammonia or organic amines or amino acids. They can also be present as zwitterions. Pharmaceutically acceptable salts and their methods of preparation are described in "Handbook of Pharmaceutical Salts, Properties, Selection and Use", P. H. Stahl, C. G. Wermuth (Eds.), Wiley-VCH 2002.

EXAMPLES

The following examples illustrate the invention.

The LC/MS analyses were carried out on a Micromass model LCT device connected to an HP 1100 device. The abundance of the product was measured using an HP G1315A diode array detector over a wave range of 200–600 nm and a Sedex 65 light scattering detector. The acquisition of the mass spectra was carried out over a range of 180 to 800. The data were analyzed using Micromass MassLynx software. Separation was carried out on a Hypersil BDS C18, 3 μm (50×4.6 mm), column, elution being carried out with a linear gradient from 5 to 90% of acetonitrile comprising 0.05% (v/v) of trifluroacetic acid (TFA) in water comprising 0.05% (v/v) of TFA over 3.5 min at a flow rate of 1 ml/min. The total time for analysis, including the period for reequilibration of the column, was 7 min.

Example 1 a) N-[1-(Quinolin-4-yl)-1H-pyrrolo[2,3-b]pyridine-3-carbonyl]guanidine

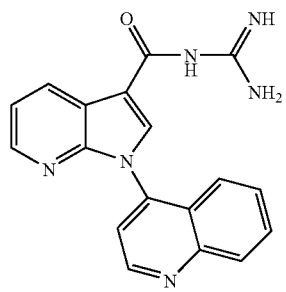

1.5 g (65 mmol) of sodium (washed beforehand in toluene) were added gradually to 100 cm³ of methanol at a temperature in the region of 20° C. under an argon atmosphere. After dissolving with stirring, 6.5 g (68 mmol) of guanidine hydrochloride were added and the mixture was stirred at a temperature in the region of 20° C. for 2 h. The reaction mixture was subsequently concentrated to dryness under reduced pressure (2.7 kPa) and the residue was twice in succession taken up in 70 cm³ of dichloromethane (stabilized over amylene) and concentrated to dryness under reduced pressure (2.7 kPa). The residue was subsequently taken up in a mixture of 50 cm³ of tetrahydrofuran and 50 cm³ of dichloromethane under an argon atmosphere at a temperature in the region of 20° C. and then 11.8 mmol of 3-chlorocarbonyl-1-(quinolin-4-yl)-1H-pyrrolo[2,3-b]pyridine hydrochloride were added thereto with stirring. After stirring at a temperature in the region of 20° C. for 15 h, the reaction mixture was concentrated to dryness under reduced pressure (2.7 kPa). The solid residue was taken up in 70 cm³ of 0.1N sodium hydroxide and the insoluble material was filtered off and then dissolved in 200 cm³ of dichloromethane. After separation by settling, the organic phase was dried over magnesium sulfate and then concentrated to dryness under reduced pressure (2.7 kPa). The residue was purified by flash chromatography on a column of silica gel (0.04–0.06 mm), elution being carried out with a dichloromethane/methanol/triethylamine (88/10/2 by volume) mixture. The fractions comprising the expected product were combined and concentrated to dryness under reduced pressure (2.7 kPa) and the solid residue was taken up in a mixture of 60 cm³ of pentane, 10 cm³ of diethyl ether and 0.1 cm³ of methanol which was brought to reflux for 10 minutes. After returning to a temperature in the region of 20° C., filtering and washing with 10 cm³ of pentane, the solid was dried at a temperature in the region of 40° C. under reduced pressure (2.7 kPa). 1.56 g of N-[1-(quinolin-4-yl)-1H-pyrrolo[2,3-b]pyridine-3-carbonyl]guanidine were thus obtained in the form of a cream solid melting at 230° C. (the product was partially salified with 3.7% of hydrochloric acid, the base form melts at 164° C.). Mass spectrum: DCI: m/z=331 MH⁺ base peak.

b) 3-Chlorocarbonyl-1-(quinolin-4-yl)-1H-pyrrolo[2,3-b]pyridine hydrochloride 50 cm³ of thionyl chloride were added to 3.4 g (11.8 mmol) of 1-(quinolin-4-yl)-1H-pyrrolo[2,3-b]pyridine-3-carboxylic acid at a temperature in the region of 20° C. under an argon atmosphere. After stirring at reflux for 2 h, the reaction mixture was concentrated to dryness under reduced pressure (2.7 kPa), triturated twice in succession with 30 cm³ of dichloromethane and then concentrated to dryness under reduced pressure (2.7 kPa) to give 11.8 mmol of 3-chlorocarbonyl-1-(quinolin-4-yl)-1H-pyrrolo[2,3-b]pyridine hydrochloride in the form of a yellow powder which was used directly in the following stage.

c) 1-(Quinolin-4-yl)-1H-pyrrolo[2,3-b]pyridine-3-carboxylic acid

A solution of 6.4 g (13 mmol) of 3-trifluoroacetyl-1-(quinolin-4-yl)-1H-pyrrolo[2,3-b]pyridine with a purity of 70% (30% of 1-(quinolin-4-yl)-1H-pyrrolo[2,3-b]pyridine) in 50 cm³ of dimethylformamide comprising 2% of water (by volume) was added with stirring, at a temperature in the region of 20° C. under an argon atmosphere, to 3 g of 75% sodium hydride (98 mmol) in 100 cm³ of dimethylformamide. The reaction medium was stirred at a temperature in the region of 20° C. for 3 h and then it was concentrated to dryness under reduced pressure (2.7 kPa). The residue was rapidly added to a mixture of 200 g of ice and 300 g of water. The precipitate obtained was filtered off and 1.2 g of 1-(quinolin-4-yl)-1H-pyrrolo[2,3-b]pyridine were thus obtained in the form of a brown solid. The pH of the aqueous filtrate was adjusted to 6 by addition of acetic acid. The brown precipitate that formed was filtered off, washed with a 2% (by volume) solution of methanol in dichloromethane and then dried under a hood for 72 h; 2.1 g of 1-(quinolin-4-yl)-1H-pyrrolo[2,3-b]pyridine-3-carboxylic acid were thus obtained in the form of a brown solid. The filtrate was separated by settling and the organic phase was dried over magnesium sulfate and then concentrated to dryness under reduced pressure (2.7 kPa) to give 0.9 g of 1-(quinolin-4-yl)-1H-pyrrolo[2,3-b]pyridine-3-carboxylic acid in the form of a brown solid. The aqueous phase was reextracted with 3 times 50 cm³ of ethyl acetate. The organic extracts were combined, dried over magnesium sulfate and concentrated to dryness under reduced pressure (2.7 kPa) and a further 0.4 g of the same compound was obtained, i.e. an overall balance of 3.4 g of 1-(quinolin-4-yl)-1H-pyrrolo[2,3-b]pyridine-3-carboxylic acid in the form of a brown solid. Mass spectrum: DCI: m/z=290 MH⁺ base peak.

d) 3-Trifluoroacetyl-1-(quinolin-4-yl)-1H-pyrrolo[2,3-b]pyridine 10 cm³ (71 mmol) of trifluoroacetic anhydride were added, under an argon atmosphere at a temperature in the region of 0° C., to 6.6 g (26.9 mmol) of 1-(quinolin-4-yl)-1H-pyrrolo[2,3-b]pyridine in 30 cm³ of dimethylformamide. After addition of the trifluoroacetic anhydride was completed, the ice bath was removed and stirring was continued at a temperature in the region of 20° C. for one hour. 25 cm³ (178 mmol) of trifluoroacetic anhydride were then added according to the same operating procedure as above and the reaction mixture was stirred at a temperature in the region of 20° C. for 4 hours. 25 cm³ (178 mmol) of trifluoroacetic anhydride were again added and stirring was continued at a temperature in the region of 20° C. for 21 hours, then 25 cm³ (178 mmol) of trifluoroacetic anhydride were added 3 times in succession every 3 hours and the reaction mixture was stirred at a temperature in the region of 20° C. for 45 h. 25 cm³ (178 mmol) of trifluoroacetic anhydride were subsequently added 3 times in succession every 3 hours. The reaction medium was subsequently stirred at a temperature in the region of 20° C. for 117 h, then it was rapidly added to 500 cm³ of water and sodium hydrogencarbonate was gradually added until a pH of 7 was reached. The mixture was extracted 4 times with 100 cm³ of ethyl acetate. The organic extracts were combined, dried over magnesium sulfate and then concentrated to dryness under reduced pressure (2.7 kPa) and 7.2 g of a brown paste comprising 50% of the expected product and 50% of the starting material were thus obtained. This paste was reacted in 30 cm³ of dimethylformamide at a temperature in the region of 20° C. with stirring: 1.1 g (13 mmol) of sodium hydrogencarbonate were added and 50 cm³ (356 mmol) of trifluoroacetic anhydride were added, then the mixture was stirred at a temperature in the region of 20° C. for 15 h. A further 1.1 g (13 mmol) of sodium hydrogencarbonate and 50 cm³ (356 mmol) of trifluoroacetic anhydride were subsequently added, the mixture being stirred at a temperature in the region of 20° C. for 5 h, and then 50 cm³ (356 mmol) of trifluoroacetic anhydride were again run in, the mixture being stirred at a temperature in the region of 20° C. for 30 h. The reaction medium was subsequently rapidly added to 500 cm³ of water and the mixture was extracted with 4 times 250 cm³ of ethyl acetate. The organic extracts were combined, dried over magnesium sulfate and then concentrated to dryness under reduced pressure (2.7 kPa). 6.6 g of 3-trifluoroacetyl-1-(quinolin-4-yl)-1H-pyrrolo[2,3-b]pyridine were thus obtained in the form of a brown solid with a purity of 70% (30% of 1-(quinolin-4-yl)-1H-pyrrolo[2,3-b]pyridine) which was used directly in the following stage. Mass spectrum: EI: m/z=341 M⁺ base peak.

e) 1-(Quinolin-4-yl)-1H-pyrrolo[2,3-b]pyridine 9 g (76.3 mmol) of 1H-pyrrolo[2,3-b]pyridine were added with stirring to 100 cm³ of dimethylformamide under an argon atmosphere at a temperature in the region of 20° C., and 2.7 g of 75% sodium hydride (84 mmol) were gradually added. After stirring at a temperature in the region of 20° C. for 10 minutes, a solution of 12.5 g (76.4 mmol) of 4-chloroquinoline in 100 cm³ of dimethylformamide was added and then the reaction mixture was heated at a temperature in the region of 100° C. for 15 h. After concentrating to dryness under reduced pressure (2.7 kPa), the residue was taken up in 300 cm³ of water. A first precipitate formed and then a second, which were filtered off. The 2 batches were combined and dissolved in 300 cm³ of dichloromethane. After separating by settling, the organic phase was dried over magnesium sulfate and concentrated to dryness under reduced pressure (2.7 kPa). The residue was purified by flash chromatography on a column of silica gel (0.04–0.06 mm), elution being carried out with a cyclohexane/ethyl acetate (50/50 by volume) mixture. The fractions comprising the expected product were combined and then concentrated to dryness under reduced pressure (2.7 kPa). 6.6 g of 1-(quinolin-4-yl)-1H-pyrrolo[2,3-b]pyridine were thus obtained in the form of a white solid. Mass spectrum: EI: m/z=245 M$^+$; base peak m/z=244 (M−H)$^+$.

Example 2 a) N-[1-(Pyridin-4-yl)-1H-pyrrolo[2,3-b]pyridine-3-carbonyl]guanidine

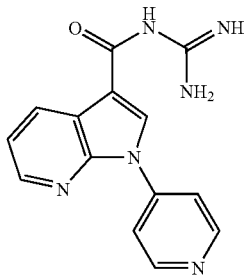

20 cm$^3$ of methanol and then a solution of 70 cm$^3$ of 0.5M sodium methoxide were added, at a temperature in the region of 20° C. under an argon atmosphere, to 3.34 g (35 mmol) of guanidine hydrochloride and the reaction mixture was stirred at a temperature in the region of 20° C. for 1 h. The reaction mixture was subsequently concentrated to dryness under reduced pressure (2.7 kPa) and the residue was 3 times in succession taken up in 20 cm$^3$ of dichloromethane (stabilized over amylene) and concentrated to dryness under reduced pressure (2.7 kPa). The residue obtained was taken up in 50 cm$^3$ of tetrahydrofuran under an argon atmosphere at a temperature in the region of 20° C. and 1.8 g (7 mmol) of 3-chlorocarbonyl-1-(pyridin-4-yl)-1H-pyrrolo[2,3-b]pyridine hydrochloride, in suspension in 50 cm$^3$ of dichloromethane, were added with stirring, followed by 50 cm$^3$ of tetrahydrofuran and 50 cm$^3$ of dichloromethane. After stirring at a temperature in the region of 20° C. for 15 h, the reaction mixture was concentrated to dryness under reduced pressure (2.7 kPa). The residue was taken up in 50 cm$^3$ of ethanol and the mixture was heated at reflux for 5 minutes and then reconcentrated to dryness under reduced pressure (2.7 kPa). The residue was purified by flash chromatography on a column of silica gel (0.04–0.06 mm), elution being carried out with an ethyl acetate/methanol/aqueous ammonia (80/20/5 by volume) mixture. The fractions comprising the expected product were combined and concentrated to dryness under reduced pressure (2.7 kPa). The residue was taken up in 30 cm$^3$ of water and the solution was basified with 1N sodium hydroxide and then 50 cm$^3$ of ethyl acetate were added. After filtration, the organic phase was separated by settling, dried over magnesium sulfate and then concentrated to dryness under reduced pressure (2.7 kPa). The residue was triturated in 20 cm$^3$ of diisopropyl ether, filtered and dried under reduced pressure (2.7 kPa) at a temperature in the region of 40° C. 45 mg of N-[1-(pyridin-4-yl)-1H-pyrrolo[2,3-b]pyridine-3-carbonyl]guanidine were thus obtained in the form of a white powder melting at 210° C. Mass spectrum: EI: m/z=280 M$^+$ base peak.

b) 3-Chlorocarbonyl-1-(pyridin-4-yl)-1H-pyrrolo[2,3-b]pyridine hydrochloride 15 cm$^3$ of thionyl chloride were added, at a temperature in the region of 25° C. under an argon atmosphere, to 1.67 g (7 mmol) of 1-(pyridin-4-yl)-1H-pyrrolo[2,3-b]pyridine-3-carboxylic acid. After stirring at reflux for 2 h, the reaction mixture was concentrated to dryness under reduced pressure (2.7 kPa). The residue was 3 times in succession triturated with 20 cm$^3$ of dichloromethane and then concentrated to dryness under reduced pressure (2.7 kPa) to give 1.8 g of 3-chlorocarbonyl-1-(pyridin-4-yl)-1H-pyrrolo[2,3-b]pyridine hydrochloride in the form of a yellow powder which was used directly in the following stage.

c) 1-(Pyridin-4-yl)-1H-pyrrolo[2,3-b]pyridine-3-carboxylic acid 0.88 g (21 mmol) of lithium hydroxide monohydrate and 25 cm$^3$ of water were added, at a temperature in the region of 20° C., to 1.8 g (7.1 mmol) of methyl 1-(pyridin-4-yl)-1H-pyrrolo[2,3-b]pyridine-3-carboxylate in solution in 25 cm$^3$ of tetrahydrofuran. After stirring at reflux of the solvent for 4 h, the reaction mixture was concentrated to dryness under reduced pressure (2.7 kPa) and the residue was taken up in 30 cm$^3$ of water (pH=10). The mixture was extracted with 30 cm$^3$ of ethyl acetate and then adjusted to pH 3 by addition of a 1N hydrochloric acid solution. The precipitate obtained was filtered off and then dried under a hood for 72 h. 1.7 g of 1-(pyridin-4-yl)-1H-pyrrolo[2,3-b]pyridine-3-carboxylate were thus obtained in the form of a white powder. Mass spectrum: EI: m/z=239 M$^+$ base peak.

d) Methyl 1-(pyridin-4-yl)-1H-pyrrolo[2,3-b]pyridine-3-carboxylate 1.76 g (10 mmol) of methyl 1H-pyrrolo[2,3-b]pyridine-3-carboxylate, 2.66 g (13 mmol) of 4-iodopyridine, 0.19 g (1 mmol) of copper(1) iodide, 4.46 g (21 mmol) of tripotassium phosphate, 1.2 cm$^3$ of a trans-1,2-cyclohexanediamine (10 mmol) and 0.5 cm$^3$ of n-dodecane were added to 100 cm$^3$ of dioxane under an argon atmosphere at a temperature in the region of 20° C. The mixture was heated at reflux of the solvent for 20 h and then it was rapidly added to a mixture of 300 cm$^3$ of ethyl acetate and 300 cm$^3$ of water. The organic phase was separated by settling, washed 3 times with 300 cm$^3$ of water and then 300 cm$^3$ of saturated aqueous sodium chloride solution, dried over magnesium sulfate and then concentrated to dryness under reduced pressure (2.7 kPa). The residue was purified by flash chromatography on a column of silica gel (0.04–0.06 mm), elution being carried out with a cyclohexane/ethyl acetate (50/50 by volume) mixture. The fractions comprising the expected product were combined and concentrated to dryness under reduced pressure (2.7 kPa) and the residue was triturated in 30 cm$^3$ of diisopropyl ether, filtered off and then dried under a hood. 1.7 g of methyl 1-(pyridin-4-yl)-1H-pyrrolo[2,3-b]pyridine-3-carboxylate were thus obtained in the form of a white powder.

Mass spectrum: EI: m/z=253 M$^+$ base peak.

e) Methyl 1H-pyrrolo[2,3-b]pyridine-3-carboxylate 4.22 g (26 mmol) of 1H-pyrrolo[2,3-b]pyridine-3-carboxylic acid were added to 100 cm$^3$ of methanol at a temperature in the region of 20° C. and then 2.5 cm$^3$ of concentrated sulfuric acid were run in dropwise. After stirring at reflux of the solvent for 16 h, the reaction medium was concentrated to dryness under reduced pressure (2.7 kPa). The residue was rapidly added to 50 cm³ of water and the pH was adjusted to 8 by addition of 1N sodium hydroxide. After extracting with 300 cm³ of ethyl acetate, the organic phase was washed with 2 times 100 cm³ of water and then 100 cm³ of saturated aqueous sodium chloride solution. After drying over magnesium sulfate and then concentrating to dryness under reduced pressure (2.7 kPa), 3.7 g of methyl 1H-pyrrolo[2,3-b]pyridine-3-carboxylate were obtained in the form of a yellow powder. Mass spectrum: EI: m/z=176 M⁺; base pic: m/z=145 (M−CH₃O)⁺.

f) 1H-Pyrrolo[2,3-b]pyridine-3-carboxylic acid 2.3 g (15.7 mmol) of 1H-pyrrolo[2,3-b]pyridine-3-carboxaldehyde and 23 cm³ (217 mmol) of 2-methyl-2-butene were added to 120 cm³ of dioxane at a temperature of 20° C. and then a solution of 2.7 g (30 mmol) of sodium chlorite and 9.2 g (66.7 mmol) of monosodium phosphate in 100 cm³ of water was added. After stirring at a temperature in the region of 20° C. for 15 h, the reaction mixture was concentrated to dryness under reduced pressure (2.7 kPa). The residue was taken up in 50 cm³ of water, filtered off, rinsed with 3 times 30 cm³ of water and then dried under a hood for 16 h. 2.2 g of 1H-pyrrolo[2,3-b]pyridine-3-carboxylic acid were thus obtained in the form of a white powder. Mass spectrum: EI: m/z=162 M⁺ base peak.

1H-Pyrrolo[2,3-b]pyridine-3-carboxaldehyde can be prepared according to patent WO 96/16964.

Example 3 a) N-[1-(Isoquinolin-1-yl)-1H-pyrrolo[2,3-b]pyridine-3-carbonyl]guanidine

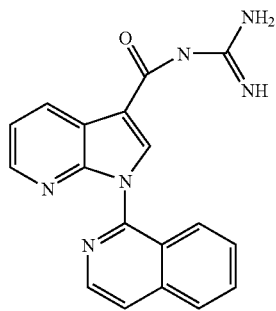

0.397 g (17.28 mmol) of sodium (washed beforehand in toluene) was gradually added to 40 cm³ of methanol at a temperature in the region of 20° C. under an argon atmosphere. After dissolving with stirring, 1.685 g (17.28 mmol) of guanidine hydrochloride were added and the mixture was stirred at a temperature in the region of 20° C. for 1 h 30. The reaction mixture was filtered and then concentrated to dryness under reduced pressure (2.7 kPa). The residue was subsequently taken up in a mixture of 70 cm³ of tetrahydrofuran and 70 cm³ of dichloromethane under an argon atmosphere at a temperature in the region of 20° C. and then 3.46 mmol of 3-chlorocarbonyl-1-(isoquinolin-1-yl)-1H-pyrrolo[2,3-b]pyridine hydrochloride were added thereto with stirring. After stirring at a temperature in the region of 20° C. for 15 h, the reaction mixture was concentrated to dryness under reduced pressure (2.7 kPa). The solid residue was taken up in 100 cm³ of water and stirred for 2 h, and then the insoluble material was filtered off. The solid was dried and then triturated in 20 cm³ of cyclohexane. The solid was filtered off and then dried at a temperature in the region of 20° C. under reduced pressure (2.7 kPa) and 0.784 g of N-[1-(isoquinolin-1-yl)-1H-pyrrolo[2,3-b]pyridine-3-carbonyl]guanidine was thus obtained in the form of a light yellow solid melting at 250° C. ¹H N.M.R. spectrum (300 MHz, (CD₃)₂SO, δ in ppm): 7.31 (dd, J=8 and 5 Hz, 1H), 7.58 (broad d, J=8.5 Hz, 1H), 7.66 (ddd, J=8.5, 7.5 and 1 Hz, 1H), 7.89 (ddd, J=8.5, 7.5 and 1 Hz, 1H), 8.09 (d, J=5.5 Hz, 1H), from 8.10 to 8.25 (mt, 2H), 8.29 (s, 1H), 8.56 (d, J=5.5 Hz, 1H), 8.90 (dd, J=8 and 1.5 Hz, 1H).

b) 3-Chlorocarbonyl-1-(isoquinolin-1-yl)-1H-pyrrolo[2,3-b]pyridine hydrochloride 0.61 cm³ (6.91 mmol) of oxalyl chloride was added, at a temperature in the region of 20° C., to 1.0 g (3.46 mmol) of 1-(isoquinolin-1-yl)-1H-pyrrolo[2,3-b]pyridine-3-carboxylic acid in suspension in 30 cm³ of dichloromethane. After stirring at a temperature in the region of 20° C. for 2 h, the reaction mixture was concentrated to dryness under reduced pressure (2.7 kPa) and used directly in the following stage.

c) 1-(Isoquinolin-1-yl)-1H-pyrrolo[2,3-b]pyridine-3-carboxylic acid

A solution of 5.20 g (15.24 mmol) of 3-trifluoroacetyl-1-(isoquinolin-1-yl)-1H-pyrrolo[2,3-b]pyridine in 100 cm³ of dimethylformamide comprising 1.8% of water (by volume) was added with stirring to 2.195 g of 60% sodium hydride (54.87 mmol) in 20 cm³ of dimethylformamide at a temperature in the region of 20° C. under an argon atmosphere. After addition of the solution was completed, the reaction medium was stirred at a temperature in the region of 20° C. for 1 h and was then concentrated to dryness under reduced pressure (2.7 kPa). The residue was rapidly added to a mixture of 200 g of ice and 200 g of water. The brown solution was filtered and then the pH of the aqueous filtrate was adjusted to 4–5 by addition of acetic acid. The mixture was stirred for 12 h and the white precipitate that formed was filtered off and then dried under a hood for 48 h. 4.82 g of 1-(isoquinolin-1-yl)-1H-pyrrolo[2,3-b]pyridine-3-carboxylate were thus obtained in the form of a light yellow solid melting at 278° C.

d) 3-Trifluoroacetyl-1-(isoquinolin-1-yl)-1H-pyrrolo[2,3-b]pyridine 12.36 cm³ (87.65 mmol) of trifluoroacetic anhydride were added to 4.3 g (17.53 mmol) of 1-(isoquinolin-1-yl)-1H-pyrrolo[2,3-b]pyridine in 50 cm³ of dimethylformamide under an argon atmosphere at a temperature in the region of 20° C. After addition of the trifluoroacetic anhydride was completed, stirring was continued at a temperature in the region of 20° C. for 12 h and then the reaction mixture was concentrated to dryness under reduced pressure (2.7 kPa) at a temperature in the region of 60° C. The residue was rapidly added to 70 cm³ of water, and sodium hydrogencarbonate was gradually added until a pH of 7–8 was reached. The solid that formed was filtered off, rinsed with 4 times 25 cm³ of water and then dried in a desiccator under reduced pressure (2.7 kPa) at a temperature in the region of 20° C. 5.31 g of 3-trifluoroacetyl-1-(isoquinolin-1-yl)-1H-pyrrolo[2,3-b]pyridine were thus obtained in the form of a brown solid melting at 210° C. which was used directly in the following stage.

e) 1-(Isoquinolin-1-yl)-1H-pyrrolo[2,3-b]pyridine 0.894 g of 60% sodium hydride (37.25 mmol) was added with stirring to 20 cm³ of dimethylformamide under an argon atmosphere at a temperature in the region of 20° C. and then a solution of 4 g (33.86 mmol) of 1H-pyrrolo[2,3-b]pyridine in 20 cm³ of dimethylformamide was gradually added. After stirring at a temperature in the region of 20° C. for 30 minutes, a solution of 5.816 g (35.55 mmol) of 1-chloroisoquinoline in 20 cm³ of dimethylformamide was added and then the reaction mixture was heated at a temperature in the region of 100° C. for 15 h. After concentrating to dryness under reduced pressure (2.7 kPa), the residue was taken up in 2 times 50 cm³ of water. The residual oil was taken up in 30 cm³ of diethyl ether. The white crystals that formed were filtered off and then dried under reduced pressure (2.7 kPa) at a temperature in the region of 20° C. 4.36 g of 1-(isoquinolin-1-yl)-1H-pyrrolo[2,3-b]pyridine were thus obtained in the form of an off-white solid melting at 87° C.

Example 4 a) N-[1-(Quinolin-2-yl)-1H-pyrrolo[2,3-b]pyridine-3-carbonyl]guanidine

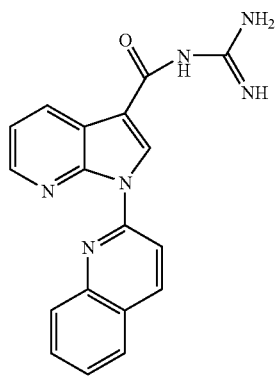

0.477 g (20.73 mmol) of sodium (washed beforehand in toluene) was gradually added to 40 cm³ of methanol at a temperature in the region of 20° C. under an argon atmosphere. After dissolving with stirring, 2.021 g (20.74 mmol) of guanidine hydrochloride were added and the mixture was stirred at a temperature in the region of 20° C. for 2 h. The reaction mixture was filtered and then concentrated to dryness under reduced pressure (2.7 kPa), and the residue was subsequently taken up in a mixture of 70 cm³ of tetrahydrofuran and 70 cm³ of dichloromethane under an argon atmosphere at a temperature in the region of 20° C. 3.46 mmol of 3-chlorocarbonyl-1-(quinolin-2-yl)-1H-pyrrolo[2,3-b]pyridine hydrochloride were added thereto with stirring. After stirring at a temperature in the region of 20° C. for 15 h, the reaction mixture was concentrated to dryness under reduced pressure (2.7 kPa). The solid residue was taken up in 100 cm³ of water and stirred for 2 h and then the insoluble material was filtered off. The solid obtained was dried and then triturated in 20 cm³ of cyclohexane. The solid was filtered off and then dried at a temperature in the region of 20° C. under reduced pressure (2.7 kPa), and 0.921 g of N-[1-(quinolin-2-yl)-1H-pyrrolo[2,3-b]pyridine-3-carbonyl]guanidine was thus obtained in the form of a light yellow solid melting at 242° C. ¹H N.M.R. spectrum (300 MHz, (CD₃)₂SO, δ in ppm): from 6.20 to 7.30 (very broad unresolved peak, 2H), 7.39 (dd, J=8 and 5 Hz, 1H), 7.63 (broad t, J=7.5 Hz, 1H), 7.84 (broad t, J=7.5 Hz, 1H), 8.03 and 8.07 (2 broad d, J=7.5 Hz, each 1H), 8.48 (dd, J=5 and 1.5 Hz, 1H), 8.64 (d, J=9 Hz, 1H), 8.89 (dd, J=8 and 1.5 Hz, 1H), 9.06 (s, 1H), 9.21 (d, J=9 Hz, 1H).

b) 3-Chlorocarbonyl-1-(quinolin-2-yl)-1H-pyrrolo[2,3-b]pyridine hydrochloride 0.606 cm³ (6.91 mmol) of oxalyl chloride was added, at a temperature in the region of 20° C., to 1.0 g (3.46 mmol) of 1-(quinolin-2-yl)-1H-pyrrolo[2,3-b]pyridine-3-carboxylic acid in suspension in 30 cm³ of dichloromethane. After stirring at a temperature in the region of 20° C. for 2 h, the reaction mixture was concentrated to dryness under reduced pressure (2.7 kPa) and the residue was used directly in the following stage.

c) 1-(Quinolin-2-yl)-1H-pyrrolo[2,3-b]pyridine-3-carboxylic acid

A solution of 5.80 g (17 mmol) of 3-trifluoroacetyl-1-(quinolin-2-yl)-1H-pyrrolo[2,3-b]pyridine in 100 cm³ of dimethylformamide comprising 1.5% of water (by volume) was added with stirring to 2.47 g of 60% sodium hydride (61.16 mmol) in 20 cm³ of dimethylformamide at a temperature in the region of 20° C. under an argon atmosphere. After addition of the solution was completed, the reaction medium was stirred at a temperature in the region of 20° C. for 3 h and was then concentrated to dryness under reduced pressure (2.7 kPa). The residue was rapidly added to a mixture of 400 g of ice and 200 g of water. The brown solution was filtered and the pH of the aqueous filtrate was adjusted to 4–5 by addition of acetic acid. The mixture was stirred for 12 h and the light brown precipitate was filtered off and then dried under a hood for 48 h. 4.85 g of 1-(quinolin-2-yl)-1H-pyrrolo[2,3-b]pyridine-3-carboxylate were thus obtained in the form of a light yellow solid melting at 275° C.

d) 3-Trifluoroacetyl-1-(quinolin-2-yl)-1H-pyrrolo[2,3-b]pyridine 14.19 cm³ (100.7 mmol) of trifluoroacetic anhydride were added to 4.94 g (20.14 mmol) of 1-(quinolin-2-yl)-1H-pyrrolo[2,3-b]pyridine in 60 cm³ of dimethylformamide under an argon atmosphere at a temperature in the region of 20° C. The reaction mixture was stirred at a temperature in the region of 20° C. for 12 h, 5.68 cm³ (40 mmol) of trifluoroacetic anhydride were added and stirring was continued at a temperature in the region of 20° C. for 60 h. A third portion of 5.68 cm³ (40 mmol) of trifluoroacetic anhydride was added and the reaction medium was stirred at a temperature in the region of 20° C. for 60 h. The reaction mixture was subsequently concentrated to dryness under reduced pressure (2.7 kPa) at a temperature in the region of 60° C. The residue was rapidly added to 100 cm³ of water, and sodium hydrogencarbonate was gradually added until a pH of 7–8 was reached. The solid that formed was filtered off, then rinsed with 4 times 25 cm³ of water and dried in a desiccator under reduced pressure (2.7 kPa) at a temperature in the region of 20° C. 5.92 g of 3-trifluoroacetyl-1-(quinolin-2-yl)-1H-pyrrolo[2,3-b]pyridine were thus obtained in the form of a brown solid melting at 198° C. which was used directly in the following stage.

e) 1-(Quinolin-2-yl)-1H-pyrrolo[2,3-b]pyridine 0.894 g of 60% sodium hydride (37.25 mmol) was added with stirring to 20 cm³ of dimethylformamide under an argon atmosphere at a temperature in the region of 20° C. and then a solution of 4 g (33.86 mmol) of 1H-pyrrolo[2,3-b]pyridine in 20 cm³ of dimethylformamide was gradually added. After stirring at a temperature in the region of 20° C. for 30 minutes, a solution of 5.816 g (35.55 mmol) of 2-chloroquinoline in 20 cm³ of dimethylformamide was added and then the reaction mixture was heated at a temperature in the region of 100° C. for 15 h. After concentrating to dryness under reduced pressure (2.7 kpa), the residue was taken up in 150 cm³ of water. The residual oil was taken up in 50 cm³ of diethyl ether. The light yellow crystals that formed were filtered off and then dried under reduced pressure (2.7 kPa) at a temperature in the region of 20° C. 4.39 g of 1-(quinolin-2-yl)-1H-pyrrolo[2,3-b]pyridine were thus obtained in the form of an off-white solid melting at 129° C.

Example 5 a) N-[1-(Pyridin-2-yl)-1H-pyrrolo[2,3-b]pyridine-3-carbonyl]guanidine hydrochloride

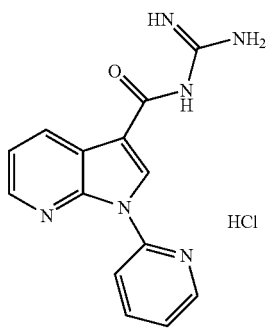

1-(Pyridin-2-yl)-1H-pyrrolo[2,3-b]pyridine-3-carboxylic acid, 0.46 g (2.4 mmol) of 1-(3-dimethylaminopropyl)-3-ethylcarbodiimide hydrochloride and 0.027 g (0,2 mmol) of 1-hydroxybenzotriazole were added to 0.59 g (10 mmol) of guanidine in 15 cm³ of tetrahydrofuran under an argon atmosphere. After stirring at a temperature in the region of 20° C. for 16 days, the reaction mixture was concentrated to dryness under reduced pressure (2.7 kPa) and the residue was triturated in 20 cm³ of methanol and then filtered. The filtrate was concentrated to dryness under reduced pressure (2.7 kPa) and the residue was purified by flash chromatography on silica gel, elution being carried out with a 100% of dichloromethane to dichloromethane/methanol/triethylamine (50/48/2 by volume) gradient over 90 min. After concentrating the fractions comprising the expected product to dryness under reduced pressure (2.7 kPa), the solid obtained was triturated in 20 cm³ of ethanol and filtered off, affording 0.028 g of N-[1-(pyridin-2-yl)-1H-pyrrolo[2,3-b]pyridine-3-carbonyl]guanidine hydrochloride in the form of a beige powder melting at 205–207° C. ¹H N.M.R. spectrum (300 MHz, (CD₃)₂SO, δ in ppm): from 7.30 to 7.45 (m, 2H), 8.08 (ddd, J=9, 8 and 2 Hz, 1H), 8.43 (dd, J=5 and 2 Hz, 1H), 8.59 (dd, J=5 and 2 Hz, 1H), 8.84 (dd, J=8 and 2 Hz, 1H), 8.89 (s, 1H), 8.95 (d, J=9 Hz, 1H).

b) 1-(Pyridin-2-yl)-1H-pyrrolo[2,3-b]pyridine-3-carboxylic acid 1.6 cm³ of 10N sodium hydroxide solution were added to methyl 1-(pyridine-2-yl)-1H-pyrrolo[2,3-b]pyridine-3-carboxylate in 15 cm³ of tetrahydrofuran. After stirring at reflux of the solvent for 200 h, the reaction mixture was acidified with 2 cm³ of 10N hydrochloric acid and then concentrated to dryness under reduced pressure (2.7 kPa) to give 1-(pyridin-2-yl)-1H-pyrrolo[2,3-b]pyridine-3-carboxylic acid in the form of a brown powder, characterized by LC/MS (m/z 240 [MH]⁺), which was used directly in the following stage.

c) Methyl 1-(Pyridn-2-yl)-1H-pyrrolo[2,3-b]pyridine-3-carboxylate 0.038 g (0.2 mmol) of cuprous iodide, 0.891 g (4.2 mmol) of potassium phosphate, 0.316 g (2 mmol) of 2-bromopyridine and 0.24 cm³ (2 mmol) of trans-1,2-cyclohexanediamine were added, under an argon atmosphere, to 0.405 g (2.3 mmol) of methyl 1H-pyrrolo[2,3-b]pyridine-3-carboxylate in solution in 0.3 cm³ of dodecane and 6 cm³ of dioxane. After stirring at a temperature in the region of 110° C. for 48 h, the reaction mixture was concentrated to dryness under reduced pressure (2.7 kPa) to give a residue which was taken up in 20 cm³ of dichloromethane. The resulting organic solution was washed with 20 cm³ of 0.1N hydrochloric acid, filtered, then dried over magnesium sulfate and concentrated to dryness under reduced pressure (2.7 kPa). Methyl 1-(pyridin-2-yl)-1H-pyrrolo[2,3-b]pyridine-3-carboxylate, characterized by LC/MS (m/z 254 [MH]⁺), was thus obtained, which was used directly in the following stage.

Example 6 a) N-[1-(4-(Methylsulfonyl)phenyl)-1H-pyrrolo[2,3-b]pyridine-3-carbonyl]guanidine hydrochloride

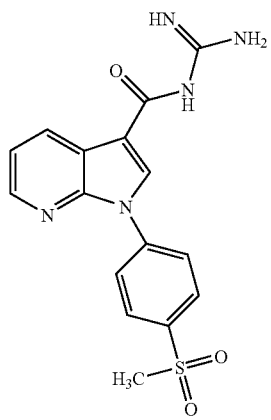

Bis[1-(4-(methylsulfonyl)phenyl)-1H-pyrrolo[2,3-b]pyridine-3-carboxylic]anhydride was added to 0.063 g (1.06 mmol) of guanidine in 15 cm³ of tetrahydrofuran under an argon atmosphere. After stirring at reflux of the solvent for 48 h, the reaction mixture was concentrated to dryness under reduced pressure (2.7 kPa). The residue was triturated in 20 cm³ of dichloromethane and filtered, and the filtrate was concentrated to dryness under reduced pressure (2.7 kPa). The residue was triturated in 20 cm³ of ethyl acetate and then filtered off. The solid obtained was recrystallized from 5 cm³ of methanol at reflux, to give 0.055 g of N-[1-(4-(methylsulfonyl)phenyl)-1H-pyrrolo[2,3-b]pyridine-3-carbonyl]guanidine hydrochloride in the form of a powder melting at 266–270° C. ¹H N.M.R. spectrum (300 MHz, (CD₃)₂SO with addition of a few drops of CD₃COOD, δ in ppm): 3.31 (s, 3H), 7.50 (dd, J=8 and 5 Hz, 1H), 8.20 (broad d, J=8.5 Hz, 2H), 8.28 (broad d, J=8.5 Hz, 2H), 8.51 (broad d, J=5 Hz, 1H), 8.63 (broad d, J=8 Hz, 1H), 8.95 (s, 1H).

b) Bis[1-(4-(methylsulfonyl)phenyl)-1H-pyrrolo[2,3-b]pyridine-3-carboxylic]anhydride 0.52 cm³ (6 mmol) of oxalyl chloride was added, under an argon atmosphere, to 1-(4-(methylsulfonyl)phenyl)-1H-pyrrolo[2,3-b]pyridine-3-carboxylic acid in 15 cm³ of dichloromethane. After stirring at a temperature in the region of 20° C. for 300 h, the reaction mixture was concentrated to dryness under reduced pressure (2.7 kPa). The residue was triturated with 20 cm³ of dichloromethane, filtered and pulled dry, and then the solid was washed with 50 cm³ of distilled water to give, after drying, 0.13 g of bis[1-(4-(methylsulfonyl)phenyl)-1H-pyrrolo[2,3-b]pyridine-3-carboxylic]anhydride in the form of a powder which was used directly in the following stage. IR spectrum (KBr): 3116, 2926, 1767, 1705, 1592, 1537, 1421, 1294, 1177, 1151, 1083, 999, 962, 775, 551 and 532 cm⁻¹.

c) 1-(4-(Methylsulfonyl)phenyl)-1H-pyrrolo[2,3-b]pyridine-3-carboxylic acid 1.6 cm³ of a 10N sodium hydroxide solution were added to methyl 1-(4-(methylsulfonyl)phenyl)-1H-pyrrolo[2,3-b]pyridine-3-carboxylate in 15 cm³ of tetrahydrofuran. After stirring at reflux of the solvent for 48 h, the reaction mixture was acidified with 2 cm³ of 10N hydrochloric acid and then concentrated to dryness under reduced pressure (2.7 kPa) to give 1-(4-(methylsulfonyl)phenyl)-1H-pyrrolo[2,3-b]pyridine-3-carboxylic acid, characterized by LC/MS (m/z 317 [MH]⁺), which was used directly in the following stage.

d) Methyl 1-(4-(methylsulfonyl)phenyl)-1H-pyrrolo[2,3-b]pyridine-3-carboxylate 0.038 g (0.2 mmol) of cuprous iodide, 0.891 g (4.2 mmol) of potassium phosphate, 0.47 g (2 mmol) of 4-bromophenyl methyl sulfone and 0.24 cm³ (2 mmol) of trans-1,2-cyclohexanediamine were added, under an argon atmosphere, to 0.405 g (2.3 mmol) of methyl 1H-pyrrolo[2,3-b]pyridine-3-carboxylate in solution in 0.3 cm³ of dodecane and 6 cm³ of dioxane. After stirring at a temperature in the region of 110° C. for 48 h, the reaction mixture was concentrated to dryness under reduced pressure (2.7 kPa) to give a residue which was taken up in 20 cm³ of dichloromethane. The resulting organic solution was washed with 20 cm³ of 0.1N hydrochloric acid and filtered, then dried over magnesium sulfate and concentrated to dryness under reduced pressure (2.7 kPa). Methyl 1-(4-(methylsulfonyl)phenyl)-1H-pyrrolo[2,3-b]pyridine-3-carboxylate, characterized by LC/MS (m/z 331 [MH]⁺), was thus obtained, which was used directly in the following stage.

Example 7 a) N-[1-(3-(Dimethylamino)phenyl)-1H-pyrrolo[2,3-b]pyridine-3-carbonyl]guanidine

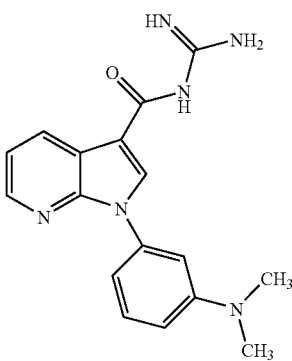

1-(3-(Dimethylamino)phenyl)-1H-pyrrolo[2,3-b]pyridine-3-carboxylic acid, 0.46 g (2.4 mmol) of 1-(3-dimethylaminopropyl)-3-ethylcarbodiimide hydrochloride and 0.027 g (0.2 mmol) of 1-hydroxybenzotriazole were added to 0.59 g (10 mmol) of guanidine in 15 cm³ of tetrahydrofuran under an argon atmosphere. After stirring at a temperature in the region of 20° C. for 16 days, the reaction mixture was concentrated to dryness under reduced pressure (2.7 kPa) and the residue was triturated in 20 cm³ of methanol and then filtered. The filtrate was concentrated to dryness under reduced pressure (2.7 kPa) and the residue was purified by flash chromatography on silica gel, elution being carried out with a 100% of dichloromethane to dichloromethane/methanol/triethylamine (50/48/2 by volume) gradient over 90 minutes. After concentrating the fractions comprising the expected product to dryness under reduced pressure (2.7 kPa), the solid obtained was triturated in 20 cm³ of ethanol and filtered off, resulting in 0.004 g of N-[1-(3-(dimethylamino)phenyl)-1H-pyrrolo[2,3-b]pyridine-3-carbonyl]guanidine in the form of a powder melting at 269–271° C. ¹H N.M.R. spectrum (300 MHz, (CD₃)₂SO with addition of a few drops of CD₃COOD, δ in ppm): 3.00 (s, 6H), 6.84 (dd, J=8.5 and 2 Hz, 1H), 7.09 (dd, J=8.5 and 2 Hz, 1H), 7.15 (t, J=2 Hz, 1H), 7.39 (t, J=8.5 Hz, 1H), 7.42 (dd, J=8 and 5 Hz, 1H), 8.46 (dd, J=5 and 2 Hz, 1H), 8.55 (dd, J=8 and 2 Hz, 1H), 8.84 (s, 1H).

b) 1-(3-(Dimethylamino)phenyl)-1H-pyrrolo[2,3-b]pyridine-3-carboxylic acid 1.6 cm³ of a 10N sodium hydroxide solution were added to methyl 1-(3-(dimethylamino)phenyl)-1H-pyrrolo[2,3-b]pyridine-3-carboxylate in 15 cm³ of tetrahydrofuran. After stirring at reflux of the solvent for 48 h, the reaction mixture was acidified with 2 cm³ of 10N hydrochloric acid and then concentrated to dryness under reduced pressure (2.7 kPa) to give 1-(3-(dimethylamino)phenyl)-1H-pyrrolo[2,3-b]pyridine-3-carboxylic acid, characterized by LC/MS (m/z 282 [MH]⁺), which was used directly in the following stage.

c) Methyl 1-(3-(dimethylamino)phenyl)-1H-pyrrolo[2,3-b]pyridine-3-carboxylate 0.038 g (0.2 mmol) of cuprous iodide, 0.891 g (4.2 mmol) of potassium phosphate, 0.40 g (2 mmol) of 3-bromo-N,N- dimethylaniline and 0.24 cm³ (2 mmol) of trans-1,2-cyclohexanediamine were added, under an argon atmosphere, to 0.405 g (2.3 mmol) of methyl 1H-pyrrolo[2,3-b]pyridine-3-carboxylate in solution in 0.3 cm³ of dodecane and 6 cm³ of dioxane. After stirring at a temperature in the region of 110° C. for 48 h, the reaction mixture was concentrated to dryness under reduced pressure (2.7 kPa) to give a residue which was taken up in 20 cm³ of dichloromethane. The resulting organic solution was washed with 20 cm³ of 0.1N hydrochloric acid and filtered, then dried over magnesium sulfate and concentrated to dryness under reduced pressure (2.7 kPa). Methyl 1-(3-(dimethylamino)phenyl)-1H-pyrrolo[2,3-b]pyridine-3-carboxylate, characterized by LC/MS (m/z 296 [MH]⁺), was thus obtained, which was used directly in the following stage.

Example 8 a) N-[1-(2-Methylquinolin-4-yl)-1H-pyrrolo[2,3-b]pyridine-3-carbonyl]guanidine hydrochloride

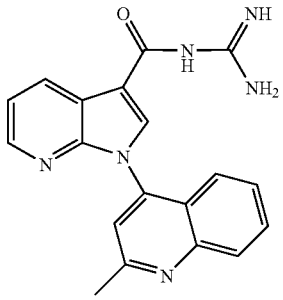

0.43 g (19 mmol) of sodium was added portionwise, at a temperature in the region of 20° C. under an argon atmosphere, to 30 cm³ of methanol and then, after the sodium has been completely consumed, 1.9 g (20 mmol) of guanidine hydrochloride were added. The reaction mixture was stirred at a temperature in the region of 20° C. for 2 h, then it was concentrated to dryness under reduced pressure (2.7 kPa) and the residue was 2 times in succession taken up in 10 cm³ of dichloromethane (stabilized over amylene) and the supernatant separated. The residue was subsequently concentrated to dryness under reduced pressure (2.7 kPa). The residue obtained was taken up in 40 cm³ of a 1:1 mixture of dichloromethane (stabilized over amylene) and tetrahydrofuran under an argon atmosphere at a temperature in the region of 20° C. and 1.1 g (3.4 mmol) of 3-chlorocarbonyl-1-(2-methylquinolin-4-yl)-1H-pyrrolo[2,3-b]pyridine hydrochloride, in suspension in 20 cm³ of a 1:1 mixture of dichloromethane (stabilized over amylene) and tetrahydrofuran, were added with stirring. After stirring at a temperature in the region of 20° C. for 65 h, the reaction mixture was concentrated to dryness under reduced pressure (2.7 kPa). The residue was taken up in 30 cm³ of ethanol and the mixture was heated at reflux for 5 minutes and then reconcentrated to dryness under reduced pressure (2.7 kPa). The residue was taken up in 50 cm³ of water and extracted successively with 50 cm³ and then 25 cm³ of ethyl acetate. The organic extracts were combined, dried over magnesium sulfate, filtered and then concentrated to dryness under reduced pressure (2.7 kPa). The residue was purified by flash chromatography on a column of silica gel (0.06–0.20 mm), elution being carried out with a dichloromethane/methanol (95/5 by volume) mixture. The fractions comprising the expected product were combined and concentrated to dryness under reduced pressure (2.7 kPa). The residue was triturated in 10 cm³ of diisopropyl ether, filtered off, washed twice with 5 cm³ of diisopropyl ether and dried under reduced pressure (2.7 kPa) at a temperature in the region of 50° C. 0.17 g of N-[1-(2-methylquinolin-4-yl)-1H-pyrrolo[2,3-b]pyridine-3-carbonyl]guanidine hydrochloride was thus obtained in the form of a yellow crystalline solid melting at 178° C. (Analysis $C_{19}H_{16}N_6O \cdot HCl$ % calculated C, 59.92; H, 4.50; N, 22.07; O, 4.20%. found C, 60.40; H, 4.50; N, 21.47).

b) 3-Chlorocarbonyl-1-(2-methylquinolin-4-yl)-1H-pyrrolo[2,3-b]pyridine hydrochloride 15.5 cm³ of thionyl chloride were added, at a temperature in the region of 25° C. under an argon atmosphere, to 1.1 g (3.6 mmol) of 1-(2-methylquinolin-4-yl)-1H-pyrrolo[2,3-b]pyridine-3-carboxylic acid. After stirring at reflux for 2 h, the reaction mixture was concentrated to dryness under reduced pressure (2.7 kPa). The residue was twice in succession triturated with 10 cm³ of dichloromethane and the supernatant removed, and then the residue was concentrated to dryness under reduced pressure (2.7 kPa). 1.1 g of 3-chlorocarbonyl-1-(2-methylquinolin-4-yl)-1H-pyrrolo[2,3-b]pyridine hydrochloride were thus obtained in the form of an orange crystalline solid which was used directly in the following stage.

c) 1-(2-Methylquinolin-4-yl)-1H-pyrrolo[2,3-b]pyridine-3-carboxylic acid 0.62 g (15 mmol) of lithium hydroxide monohydrate and 18 cm³ of water were added, at a temperature in the region of 20° C., to 1.6 g (5.0 mmol) of methyl 1-(2-methylquinolin-4-yl)-1H-pyrrolo[2,3-b]pyridine-3-carboxylate in solution in 18 cm³ of tetrahydrofuran. After stirring at reflux of the solvent for 4 h, the reaction mixture was concentrated to dryness under reduced pressure (2.7 kPa) and the residue was taken up in 80 cm³ of water. The mixture was extracted with 30 cm³ of ethyl acetate and then the pH was adjusted to 3 by addition of 14 cm³ of a 1N hydrochloric acid solution. The precipitate obtained was filtered off, washed twice with 10 cm³ of water, pulled dry and then dried in a desiccator under reduced pressure at a temperature in the region of 20° C. for 4 days and under reduced pressure (2.7 kPa) at a temperature in the region of 50° C. for 12 h. 1.1 g of 1-(2-methylquinolin-4-yl)-1H-pyrrolo[2,3-b]pyridine-3-carboxylic acid were thus obtained in the form of a yellow crystalline powder melting at a temperature of greater than 260° C. used directly in the following stage.

d) Methyl 1-(2-methylquinolin-4-yl)-1H-pyrrolo[2,3-b]pyridine-3-carboxylate 5.5 g (31 mmol) of 4-chloro-2-methylquinoline and 8.9 g (65 mmol) of potassium carbonate were added to 4.6 g (26 mmol) of methyl 1H-pyrrolo[2,3-b]pyridine-3-carboxylate in 93 cm³ of dimethyl sulfoxide under argon. The reaction mixture was heated at a temperature in the region of 120° C. for 16 h, then it was cooled to a temperature in the region of 20° C. and treated with 250 cm³ of water. The aqueous phase was extracted with 250 cm³ and then 125 cm³ of ethyl acetate. The organic extracts were combined, dried over magnesium sulfate, filtered and then concentrated to dryness under reduced pressure (2.7 kPa). The residue was purified by flash chromatography on a column of silica gel (0.04–0.06 mm), elution being carried out with dichloromethane. The fractions comprising the expected product were combined and then concentrated to dryness under reduced pressure (2.7 kPa). 1.4 g of methyl 1-(2-methylquinolin-4-yl)-1H-pyrrolo[2,3-b]pyridine-3-carboxylate were thus obtained in the form of an orange crystalline solid melting at 179° C.

Example 9 a) N-[1-(7-Methyl-7H-pyrrolo[2,3-d]pyrimidin-4-yl)-1H-pyrrolo[2,3-b]pyridine-3-carbonyl]-guanidine

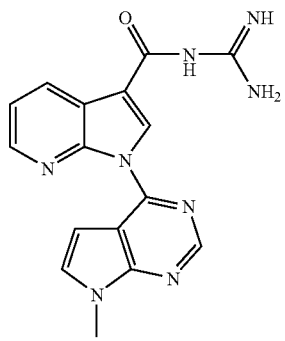

To 40 cm³ of methanol at about 20° C. under argon atmosphere, was added portionwise 0.36 g (16 mmol) of sodium. Then, after total consumption of the latter, 1.5 g (16 mmol) of guanidine hydrochloride were added. The reaction mixture was stirred at about 20° C. for 1.5 hours and filtered. The precipitate was washed with 5 cm³ of methanol and the combined filtrates were concentrated to dryness in vacuo (2.7 kPa). The residue was diluted in 30 cm³ of dichloromethane and concentrated to dryness in vacuo (2.7 kPa). The residue was diluted in 70 cm³ of tetrahydrofuran under argon atmosphere at about 20° C. and a suspension of 1.3 g (3.2 mmol) of 3-chlorocarbonyl-1-(7-methyl-7H-pyrrolo[2,3-d]pyrimidin-4-yl)-1H-pyrrolo[2,3-b]pyridine in 70 cm³ of dichloromethane was added. The reaction mixture was stirred at about 20° C. for 60 hours and then concentrated to dryness in vacuo (2.7 kPa). The residue was diluted in 100 cm³ of water and the off-white precipitate was filtered and washed twice with 10 cm³ of water. The solid was dried in vacuo at about 50° C. and then recrystallized from 30 cm³ of methanol. The precipitate was washed twice with 5 cm³ of methanol and once with 10 cm³ of diisopropylether respectively, and dried in vacuo at about 50° C. to yield 0.45 g of N-[1-(7-methyl-7H-pyrrolo[2,3-d]pyrimidin-4-yl)-1H-pyrrolo[2,3-b]pyridine-3-carbonyl]-guanidine as a gray cristalline powder: mp>260° C. IR spectrum (KBr): 3425; 3157; 1590; 1558; 1518; 1449; 1418; 1308; 1216; 1009; 805; 770; 723; 702 and 605 cm⁻¹. Mass spectrum (EI): m/e 334 M+., m/e 276 (M–CH₄N₃)⁺. (base peak), m/e 145 (m/e=276–C₇H₅N₃)⁺, m/e 132 (C₇H₆N₃)⁺.

b) 3-Chlorocarbonyl-1-(7-methyl-7H-pyrrolo[2,3-d]pyrimidin-4-yl)-1H-pyrrolo[2,3-b]pyridine To 0.93 g (3.2 mmol) of 1-(7-methyl-7H-pyrrolo[2,3-d]pyrimidin-4-yl)-1H-pyrrolo[2,3-b]pyridine-3-carboxylic acid in 20 cm³ of chloroform at about 20° C. and under argon atmosphere, was added dropwise 10 cm³ (0.14 mol) of thionyl chloride. The reaction mixture was then heated and stirred at reflux temperature for 1 hour, and then it was cooled to about 20° C. and concentrated to dryness in vacuo (2.7 kPa). The residue was taken up in 20 cm³ of chloform (2.7 kPa) and concentrated to dryness in vacuo (2.7 kPa) to yield 1.25 g of 3-chlorocarbonyl-1-(7-methyl-7H-pyrrolo[2,3-d]pyrimidin-4-yl)-1H-pyrrolo[2,3-b]pyridine as a yellow powder which was used directly in the next step.

c) 1-(7-Methyl-7H-pyrrolo[2,3-d]pyrimidin-4-yl)-1H-pyrrolo[2,3-b]pyridine-3-carboxylic acid To 1.2 g (3.7 mmol) of methyl 1-(7-methyl-7H-pyrrolo[2,3-d]pyrimidin-4-yl)-1H-pyrrolo[2,3-b]pyridine-3-carboxylate were successively added 13.5 cm³ of tetrahydrofuran, 0.47 g (11.2 mmol) of lithium hydroxide, monohydrate and 13.5 cm³ of distilled water. The reaction mixture was heated at reflux temperature for 4 hours and then concentrated to dryness in vacuo (2.7 kPa). The residue was dissolved into 72 cm³ of distilled water and the mixture was extracted with 35 cm³ of ethyl acetate. The aqueous phase was cooled to about 5° C. and 10 cm³ of 1N hydrochloric acid were added dropwise (pH ca. 3). The resulting precipitate was filtered, washed twice with 20 cm³ of distilled water and dried in vacuo at about 50° C. to yield 0.93 g of 1-(7-methyl-7H-pyrrolo[2,3-d]pyrimidin-4-yl)-1H-pyrrolo[2,3-b]pyridine-3-carboxylic acid as off-white crystals. mp>260° C.; IR spectrum (KBr): 3461; 3152; 2951; 2571; 1678; 1590; 1544; 1452; 1263; 1204; 916; 808; 774; 746; 681 and 607 cm⁻¹.

d) Methyl 1-(7-methyl-7H-pyrrolo[2,3-d]pyrimidin-4-yl)-1H-pyrrolo[2,3-b]pyridine-3-carboxylate To 1.9 g (9.2 mmol) of methyl 1H-pyrrolo[2,3-b]pyridine-3-carboxylate in 50 cm³ of dimethylsulfoxyde under argon atmosphere, were added 1.85 g (11.0 mmol) of 4-chloro-7-methyl-7H-pyrrolo[2,3-d]pyrimidine, followed by 3.2 g (23.0 mmol) of potassium carbonate. The reaction mixture was heated at about 120° C. for 24 hours, upon which it was cooled to about 20° C. and treated with 200 cm³ of distilled water. The mixture was then treated with 300 cm³ and 150 cm³ of ethyl acetate and filtered on Celite®. The aqueous phase was extracted with 150 cm³ of ethyl acetate. The combined organic extracts were dried on magnesium sulfate and concentrated to dryness in vacuo (2.7 kPa). The residue was purified via column chromatography on silica gel (0,04–0,06 mm), with dichloromethane/methanol 99:1 v/v as eluting solvent. Thus, 1.25 g of methyl 1-(7-methyl-7H-pyrrolo[2,3-d]pyrimidin-4-yl)-1H-pyrrolo[2,3-b]pyridine-3-carboxylate were obtained as a light-yellow crystalline powder. mp: 207° C.

4-Chloro-7-methyl-7H-pyrrolo[2,3-d]pyrimidine can be prepared as described in patent application WO2004007479.

Example 10

N-[1-(2-Hydroxy-quinolin-4-yl)-1H-pyrrolo[2,3-b]pyridine-3-carbonyl]-guanidine

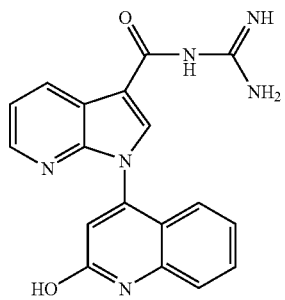

4.8 mg of N-(1-quinolin-4-yl-1H-pyrrolo[2,3-b]pyridine-3-carbonyl)-guanidine were dissolved using 150 ml of an aqueous solution containing 381 mg MgCl$_2$, 1.3 mM NADPH (Dihydronicotinamide adenine dinucleotide phosphate, Calbiochem product number: 481973; Shen, A. L., et al. 1989. J. Biol. Chem. 264, 7584; Yamano, S., et al. 1989. Mol. Pharmacol. 36, 83.), 300 mg of human S9 fraction and 2.5 mM UDPGA (Uridine 5'-diphosphoglucuronic acid trisodium salt, Sigma catalog number U6751). The mixture was incubated for 120 minutes at 37° C. Then, 40 ml of acetonitrile were added, proteins centrifuged and decanted. This solution was concentrated to 100 ml and chromatographed using the system described below. The solvents were removed under reduced pressure to yield 0.9 mg of N-[1-(2-hydroxy-quinolin-4-yl)-1H-pyrrolo[2,3-b]pyridine-3-carbonyl]-guanidine as an amorphous solid.

Preparative HPLC was carried out as follows:
column: Merck Purospher RP18 HC, 5 µm, 125–25
mobile phase
solv. A: purified water+0.5% acetonitrile+0.1% formic acid
solv. B: acetonitrile+5% purified water
flow rate: 30 mL/min
isocratic conditions
solv. A:solv. B=82:18

NHE Inhibition Method

The NHE inhibitory activities (IC$_{50}$ values) of the compounds according to the invention were determined by a FLIPR test.

The test is performed in the FLIPR (Fluorescent Imaging Plate Reader) equipped with clear-bottomed and black-walled 96-well microtitration plates. The transfected cell lines expressing the various NHE subtypes (the parental cell line LAP-1 shows no endogenous NHE activity as a result of mutagenesis and subsequent selection) are seeded the preceding day at a density of ~25 000 cells/well.

The growth medium for the transfected cells (Iscove+10% foetal calf serum) also comprises G418 as selection antibiotic to ensure the presence of transfected sequences.

The actual test begins by eliminating the growth medium and adding 100 µl of loading buffer per well (5 µM of BCECF-AM [2',7'-bis(2-carboxyethyl)-5-(6)-carboxyfluoresceine acetoxymethyl ester] in 20 mM of NH$_4$Cl, 115 mM of choline chloride, 1 mM of CaCl$_2$, 5 mM of KCl, 20 mM of HEPES and 5 mM of glucose; pH 7.4 (adjusted with KOH). The cells are then incubated for 20 minutes at 37° C.

This incubation results in the loading of the fluorescent dye into the cells, the fluorescence intensity of which depends on the pH$_i$, and on the NH$_4$Cl, which results in a slight basification of the cells.

The precursor BCECF-AM, a non-fluorescent dye, is, as an ester, capable of crossing the membrane. The actual dye, which is incapable of crossing the membrane, is released inside the cell by esterases.

After this 20-minute incubation, the loading buffer, which comprises NH$_4$Cl and free BCECF-AM, is removed by washing three times in the cell washing device (Tecan Columbus), each wash being performed with 400 µl of washing buffer (133.8 mM of choline chloride, 4.7 mM of KCl, 1.25 mM of MgCl$_2$, 1.25 mM of CaCl$_2$, 0.97 mM of K$_2$HPO$_4$, 0.23 mM of KH$_2$PO$_4$, 5 mM of HEPES and 5 mM of glucose; pH 7.4 (adjusted with KOH)). The residual volume remaining in the wells is 90 µl (possibly between 50 and 125 µl). This washing step removes the free BCECF-AM and results in an intracellular acidification (pH$_i$ of 6.3–6.4) due to the removal of the external ammonium ions.

As the equilibrium of the intracellular ammonium with the aqueous ammonia and the protons, by removal of the extracellular ammonium and by the subsequent immediate crossing of the aqueous ammonia across the cell membrane, is disrupted, the washing process results in intracellular protons remaining, which is the cause of the intracellular acidification. This acidification can result finally in the death of the cells if it lasts long enough. It is important here for the washing buffer to be free of sodium (<1 mM), otherwise the extracellular sodium ions would result in an immediate increase in the pH$_i$ on account of the activity of the cloned NHE isoforms. It is also important for all the buffers used (loading buffer, washing buffer and regeneration buffer) not to contain any HCO$_3^-$ ions, otherwise the presence of bicarbonate would result in the activation of bicarbonate-dependent systems that disrupt the pH$_i$ regulation, which systems are contained in the LAP-1 parental cell line.

The microtiter plates containing acidified cells are then transferred (up to 20 minutes after the acidification) to the FLIPR. In the FLIPR, the intracellular fluorescent dye is activated with light of a wavelength of 488 nm, which is generated by an argon laser, and the measuring parameters (laser power, illumination time and diaphragm of the CDD camera integrated into the FLIPR) are chosen such that the average value of the fluorescent signal per well is between 30,000 and 35,000 relative fluorescence units.

The actual measurement in the FLIPR starts with a photograph being taken by the CCD camera every two seconds under software control. After 10 seconds, the increase in the intracellular pH is initiated by adding 90 µl. of regeneration buffer (133.8 mM of NaCl, 4.7 mM of KCl, 1.25 mM of MgCl$_2$, 1.25 mM of CaCl$_2$, 0.97 mM of K$_2$HPO$_4$, 0.23 mM of KH$_2$PO$_4$, 10 mM of HEPES and 5 mM of glucose; pH 7.4 (adjusted with NaOH)) using a 96-well pipette device incorporated into the FLIPR. Some wells, to which is added pure regeneration buffer, serve as positive controls (100% NHE activity). The negative controls (0% NHE activity) contain washing buffer. Regeneration buffer with twice the concentration of test substance is added to all the other wells. Measurement in the FLIPR terminates after 60 measurements (two minutes).

The experimental data allow the NHE activities to be calculated for each concentration of test substance and, from these, the IC$_{50}$ values of the substances. For the NHE1 subtype the following results were obtained.

| example No. | IC50 (NHE1)/μM |
|---|---|
| 1 | 0.003 |
| 2 | 0.010 |
| 3 | 0.015 |
| 4 | 6.24 |
| 5 | 0.018 |
| 6 | 3.76 |
| 7 | 0.003 |
| 8 | 0.026 |
| 9 | 0.037 |
| 10 | 0.66 |

The present invention also relates to the use of compounds of formula I for preparing a medicament and to pharmaceutical compositions comprising, as active principle, a compound of formula I, or a tautomer or a pharmaceutically acceptable salt thereof. The invention relates also to the use of the compounds of formula I and/or pharmaceutically acceptable salts thereof for the preparation of medicaments and pharmaceutical compositions as inhibitors of the NHE. Claimed is a medicine for human, veterinary or phytoprotective use, comprising an effective amount of a compound of formula I and/or the pharmaceutically acceptable salts thereof, together with pharmaceutically acceptable carriers and additives, alone or in combination with other active pharmaceutical ingredients or medicaments.

The pharmaceutical compositions according to the invention consist of a compound of formula I and/or the pharmaceutically acceptable salt thereof, in pure form or in the form of a composition in which it is combined with any other pharmaceutically compatible product, which may be inert or physiologically active. The medicaments according to the invention can be administered, for example, orally, parenterally, intravenously, rectally, transdermally, topically or by inhalation. The medicaments generally comprise active ingredients of the formula I and/or pharmaceutically acceptable salts therof in an amount of from 0.001 mg to 1 g per dose unit.

The excipients suitable for the desired pharmaceutical formulation are familiar to the skilled worker on the basis of his expert knowledge. Besides solvents, gel formers, suppository bases, tablet excipients, and other active ingredient carriers, it is possible to use, for example, antioxidants, dispersants, emulsifiers, antifoams, flavourings, preservatives, solubilizers or colors.

For a pharmaceutical formulation for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for the preparation to take place both as dry granules and as wet granules. Examples of suitable oily carriers or solvents are vegetable or animal oils such as sunflower oil or fish liver oil.

Tablets, pills, powders (gelatine capsules or cachets) or granules can be used as solid compositions for oral administration. In these compositions, the active principle according to the invention is mixed with one or more inert diluents, such as starch, cellulose, sucrose, lactose or silica, under a stream of argon. These compositions may also comprise substances other than diluents, for example one or more lubricants, such as magnesium stearate or talc, a colorant, a coating (dragees) or a varnish.

Pharmaceutically acceptable solutions, suspensions, emulsions, syrups and elixirs comprising inert diluents, such as water, ethanol, glycerol, plant oils or liquid paraffin, can be used as liquid compositions for oral administration. These compositions may comprise substances other than diluents, for example wetting products, sweeteners, thickeners, flavourings or stabilisers.

The sterile compositions for parenteral administration may preferably be aqueous or non-aqueous solutions, suspensions or emulsions. Solvents or vehicles that can be used include water, propylene glycol, a polyethylene glycol, plant oils, in particular olive oil, injectable organic esters, for example ethyl oleate, or other suitable organic solvents. These compositions may also comprise adjuvants, in particular wetting agents, tonicity agents, emulsifiers, dispersants and stabilisers. The sterilisation may be performed in several ways, for example by aseptic filtration, by incorporating sterilising agents into the composition, by irradiation or by heating. They may also be prepared in the form of sterile solid compositions that may be dissolved at the time of use in sterile water or any other injectable sterile medium.

The compositions for rectal administration are suppositories or rectal capsules that comprise, besides the active product, excipients, such as cocoa butter, semi-synthetic glycerides or polyethylene glycols.

The compositions for topical administration may be, for example, creams, lotions, eye drops, mouthwashes, nasal drops or aerosols.

For subcutaneous, intramuscular or intravenous administration, the active compounds used are converted, if desired with the substances customary for this purpose, such as solubilizers, emulsifiers or other excipients, into a solution, suspension or emulsion. Examples of suitable solvents are: water, physiological saline or alcohols, e.g. ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the active ingredient of formula I and/or the pharmaceutically acceptable salts thereof in a pharmaceutically acceptable solvent such as, in particular, ethanol or water, or a mixture of such solvents. The formulation may, if required, also contain other pharmaceutical excipients such as surfactants, emulsifiers and stabilizers, and a propellant gas. Such a preparation contains, for example, the active ingredient in a concentration of about 0.1 to 10, in particular of about 0.3 to 3% by weight.

The dosage of the active ingredient of formula I to be administered, and the frequency of administration, depend on the desired effect, the potency and duration of action of the compounds used; additionally also on the nature and severity of the disorder to be treated and on the sex, age, weight and individual responsiveness of the mammal to be treated. In general, the physician will determine the appropriate dosage as a function of the age and weight and all the other factors specific to the individual to be treated.

On average, the daily dose of a compound of formula I and/or the pharmaceutically acceptable salts thereof for a patient weighing about 75 kg is at least 0.001 mg/kg, preferably 1 mg/kg, to a maximum of 1000 mg/kg, preferably 100 mg/kg, of body weight. For acute episodes of the disorder, for example immediately after suffering a myocardial infarction, higher and, in particular, more frequent dosages may also be necessary, e.g. up to 4 single doses a day. Up to 2000 mg a day may be necessary, in particular on i.v. administration, for example for a patient with infarction in the intensive care unit, and the compounds of the invention can be administered by infusion.

The following examples illustrate compositions according to the invention:

Example A

Gel capsules containing a 50 mg dose of active product, having the composition below, can be prepared according to the usual technique:

| | |
|---|---|
| Compound of the formula (I) | 50 mg |
| Cellulose | 18 mg |
| Lactose | 55 mg |
| Colloidal silica | 1 mg |
| Sodium carboxymethyl starch | 10 mg |
| Talc | 10 mg |
| Magnesium stearate | 1 mg |

Example B

Tablets comprising a 50 mg dose of active product, having the composition below, can be prepared according to the usual technique:

| | |
|---|---|
| Compound of the formula (I) | 50 mg |
| Lactose | 104 mg |
| Cellulose | 40 mg |
| Polyvidone | 10 mg |
| Sodium carboxymethyl starch | 22 mg |
| Talc | 10 mg |
| Magnesium stearate | 2 mg |
| Colloidal silica | 2 mg |
| Mixture of hydroxymethylcellulose, glycerol and titanium oxide (72/3.5/24.5) qs 1 finished film-coated tablet weighing | 245 mg |

Example C

An injectable solution comprising 10 mg of active product, having the composition below, can be prepared:

| | |
|---|---|
| Compound of the formula (I) | 10 mg |
| Benzoic acid | 80 mg |
| Benzyl alcohol | 0.06 ml |
| Sodium benzoate | 80 mg |
| 95% ethanol | 0.4 ml |
| Sodium hydroxide | 24 mg |
| Propylene glycol | 1.6 ml |
| Water qs | 4 ml |

What is claimed is:
1. A compound of formula I

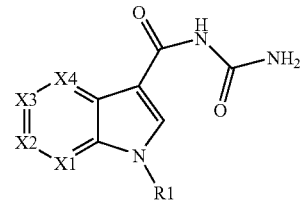

wherein
   $X_1$ is N;
   $X_2$, $X_3$ and $X_4$ are; $CR_2$;
   $R_2$ is H, F, Cl, Br, I, alkyl having 1, 2, 3, 4, 5 or 6 carbon atoms, cycloalkyl having 3, 4, 5, 6 or 7 carbon atoms, polyfluoroalkyl having 1, 2, 3 or 4 carbon atoms, $SO_2$alkyl having 1, 2, 3, 4, 5 or 6 carbon atoms, NRaRb, hydroxyl, alkoxy having 1, 2, 3, 4, 5 or 6 carbon atoms, hydroxyalkyl having 1, 2, 3, 4, 5 or 6 carbon atoms or dialkylaminoalkyl with each alkyl having independently 1, 2, 3, 4, 5 or 6 carbon atoms;
   R1 is aryl, alkyl having 1, 2, 3, 4, 5 or 6 carbon atoms, cycloalkyl having 3, 4, 5, 6 or 7 carbon atoms, polyfluoroalkyl having 1, 2, 3 or 4 carbon atoms, arylalkyl with alkyl having 1, 2, 3 or 4 carbon atoms, heteroarylalkyl with alkyl having 1, 2, 3 or 4 carbon atoms or heteroaryl,
      wherein said aryl or heteroaryl is optionally substituted by one or more substituents selected from the group consisting of alkyl having 1, 2, 3, 4, 5 or 6 carbon atoms, cycloalkyl having 3, 4, 5, 6 or 7 carbon atoms, F, Cl, Br, I, $NO_2$, $NH_2$, alkylamino with alkyl having 1, 2, 3, 4, 5 or 6 carbon atoms, NRaRb, alkylcarbonylamino having 1, 2, 3, 4, 5 or 6 carbon atoms, hydroxyl, alkoxy having 1, 2, 3, 4, 5 or 6 carbon atoms, $S(O)_nR_3$, $CO_2H$, alkoxycarbonyl having 1, 2, 3, 4, 5 or 6 carbon atoms, alkylcarbonyl having 1, 2, 3, 4, 5 or 6 carbon atoms, $CONH_2$, CONRaRb, alkylsulfonylamino with alkyl having 1, 2, 3, 4, 5 or 6 carbon atoms, cyano, polyfluoroalkyl having 1, 2, 3 or 4 carbon atoms, polyfluoroalkoxy having 1, 2 or 3 carbon atoms and $SO_3H$;
   n is 0,1 or 2;
   Ra and Rb are, independently of one another, alkyl having 1, 2, 3, 4, 5 or 6 carbon atoms, or
   Ra and Rb form together with the nitrogen atom to which they are attached, a 5- or 6-membered heterocycle which can optionally contain another heteroatom chosen from the group consisting of O, S and N; and
   $R_3$ is alkyl having 1, 2, 3, 4, 5 or 6 carbon atoms, alkylamino having 1, 2, 3, 4, 5 or 6 carbon atoms or $NH_2$; or
   a racemate, an enantiomer or a diastereomer thereof, or mixtures thereof, a tautomers thereof, or a pharmaceutically acceptable salt thereof.
2. The compound of formula I according to claim 1, wherein
   $X_1$ is N;
   $X_2$, $X_3$ and $X_4$ are $CR_2$;
   $R_2$ is H; and
   R1 is aryl or heteroaryl,
      wherein said aryl or heteroaryl is optionally substituted by one or more substituents selected from the group consisting of alkyl having 1, 2, 3, 4, 5 or 6 carbon atoms, cycloalkyl having 3, 4, 5, 6 or 7 carbon atoms, F, Cl, Br, I, $NO_2$, $_{NH2}$, alkylamino with alkyl having 1, 2, 3, 4, 5 or 6 carbon atoms, NRaRb, alkylcarbonylamino having 1, 2, 3, 4, 5 or 6 carbon atoms, hydroxyl, alkoxy having 1, 2, 3, 4, 5 or 6 carbon atoms, $S(O)_nR_3$, $CO_2H$, alkoxycarbonyl having 1, 2, 3, 4, 5 or 6 carbon atoms, alkylcarbonyl having 1, 2, 3, 4, 5 or 6 carbon atoms, $CONH_2$, CONRaRb, alkylsulfonylamino with alkyl having 1, 2, 3, 4, 5 or 6 carbon atoms, cyano, polyfluoroalkyl having 1, 2, 3 or 4 carbon atoms, polyfluoroalkoxy having 1, 2 or 3 carbon atoms and $SO_3H$.

3. The compound of formula I according to claim 2, wherein

R1 is aryl or heteroaryl selected from the group of pyridine, pyrimidine, pyrazine, thiazole, imidazole, quinoline, isoquinoline, cinnoline, quinazoline, naphthyridine, quinoxaline, benzothiazole, benzimidazole, indole, 7-azaindole and pyrrolo[2,3-d]pyrimidine, wherein said aryl or heteroaryl is optionally substituted by one or more substituents selected from the group consisting of alkyl having 1, 2, 3, 4, 5 or 6 carbon atoms, cycloalkyl having 3, 4, 5, 6 or 7 carbon atoms, F, Cl, Br, I, $NO_2$, $NH_2$, alkylamino with alkyl having 1, 2, 3, 4, 5 or 6 carbon atoms, NRaRb, alkylcarbonylamino having 1, 2, 3, 4, 5 or 6 carbon atoms, hydroxyl, alkoxy having 1, 2, 3, 4, 5 or 6 carbon atoms, $S(O)_nR_3$, $CO_2H$, alkoxycarbonyl having 1, 2, 3, 4, 5 or 6 carbon atoms, alkylcarbonyl having 1, 2, 3, 4, 5 or 6 carbon atoms, $CONH_2$, CONRaRb, alkylsulfonylamino with alkyl having 1, 2, 3, 4, 5 or 6 carbon atoms, cyano, polyfluoroalkyl having 1, 2, 3 or 4 carbon atoms, polyfluoroalkoxy having 1, 2 or 3 carbon atoms and $SO_3H$.

4. The compound of formula I according to claim 3, wherein $X_1$ is N

R1 is phenyl or heteroaryl selected from the group consisting of pyridine, pyrimidine, pyrazine, thiazole, imidazole, quinoline, isoquinoline, cinnoline, quinazoline, naphthyridine, quinoxaline, benzothiazole, benzimidazole, indole, 7-azaindole and pyrrolo[2,3-d]pyrimidine, wherein said phenyl or heteroaryl is optionally substituted by one or more substituents selected from the group consisting of alkyl having 1, 2, 3, 4, 5 or 6 carbon atoms, $NH_2$, NRaRb, hydroxyl and $S(O)_nR_3$;

n is 2;

Ra and Rb are, independently of one another, alkyl having 1, 2, 3, 4, 5 or 6 carbon atoms; and $R_3$ is alkyl having 1, 2, 3, 4, 5 or 6 carbon atoms;

and racemates, enantiomers and diastereomers and mixtures thereof, tautomers thereof and pharmaceutically acceptable salts thereof.

5. The compound of formula I according to claim 4 selected from the group consisting of:

N-[1-quinolin-3-yl)-1H-pyrrolo[2,3-b]pyridine-3-carbonyl]guanidine,

N-[1-quinolin-5-yl)-1H-pyrrolo[2,3-b]pyridine-3-carbonyl]guanidine,

N-[1-quinolin-6-yl)-1H-pyrrolo[2,3-b]pyridine-3-carbonyl]guanidine,

N-[1-quinolin-7-yl)-1H-pyrrolo[2,3-b]pyridine-3-carbonyl]guanidine,

N-[1-quinolin-8-yl)-1H-pyrrolo[2,3-b]pyridine-3-carbonyl]guanidine,

N-[1-(isoquinolin-5-yl)-1H-pyrrolo[2,3-b]pyridine-3-carbonyl]guanidine,

N-[1-(cinnolin-4-yl)-1H-pyrrolo[2,3-b]pyridine-3-carbonyl]guanidine,

N-[1-(quinazolin-4-yl)-1H-pyrrolo[2,3-b]pyridine-3-carbonyl]guanidine,

N-[1-(quinazolin-7-yl)-1H-pyrrolo[2,3-b]pyridine-3-carbonyl]guanidine,

N-[1-(2-methylquinazolin-4-yl)-1H-pyrrolo[2,3-b]pyridine-3-carbonyl]guanidine,

N-[1-(1,5-naphthyridin-4-yl)-1H-pyrrolo[2,3-b]pyridine-3-carbonyl]guanidine,

N-[1-(1,6-naphthyridin-4-yl)-1H-pyrrolo[2,3-b]pyridine-3-carbonyl]guanidine,

N-[1-(1,7-naphthyridin-4-yl)-1H-pyrrolo[2,3-b]pyridine-3-carbonyl]guanidine,

N-[1-(1,8-naphthyridin-4-yl)-1H-pyrrolo[2,3-b]pyridine-3-carbonyl]guanidine,

N-[1-(2-amino-1,8-naphthyridin-4-yl)-1H-pyrrolo[2,3-b]pyridine-3-carbonyl]guanidine, N-[1-(quinoxalin-5-yl)-1H-pyrrolo[2,3-b]pyridine-3-carbonyl]guanidine, N-[1-(pyridin-3-yl)-1H-pyrrolo[2,3-b]pyridine-3-carbonyl]guanidine, N-[1-(pyrimidin-2-yl)-1H-pyrrolo[2,3-b]pyridine-3-carbonyl]guanidine, N-[1-(pyrimidin-4-yl)-1H-pyrrolo[2,3-b]pyridine-3-carbonyl]guanidine, N-[1-(pyrimidin-5-yl)-1H-pyrrolo[2,3-b]pyridine-3-carbonyl]guanidine, N-[1-(pyrazin-2-yl)-1H-pyrrolo[2,3-b]pyridine-3-carbonyl]guanidine, N-[1-(benzothiazol-4-yl)-1H-pyrrolo[2,3-b]pyridine-3-carbonyl]guanidine, N-[1-(benzimidazol-4-yl)-1H-pyrrolo[2,3-b]pyridine-3-carbonyl]guanidine, N-[1-(indol-4-yl)-1H-pyrrolo[2,3-b]pyridine-3-carbonyl]guanidine, N-[1-(indol-5-yl)-1H-pyrrolo[2,3-b]pyridine-3-carbonyl]guanidine, N-[1-(1-(methylsulfonyl)indol-4-yl)-1H-pyrrolo[2,3-b]pyridine-3-carbonyl]guanidine, N-[1-(7-azaindol-4-yl)-1H-pyrrolo[2,3-b]pyridine-3-carbonyl]guanidine, N-[1-(pyrrolo[2,3-d]pyrimidin-4-yl)-1H-pyrrolo[2,3-b]pyridine-3-carbonyl]guanidine, N-[1-(7-methylpyrrolo[2,3-d]pyrimidin-4-yl)-1H-pyrrolo[2,3-b]pyridine-3-carbonyl]guanidine, N-[1-(thiazol-2-yl)-1H-pyrrolo[2,3-b]pyridine-3-carbonyl]guanidine, N-[1-(imidazol-2-yl)-1H-pyrrolo[2,3-b]pyridine-3-carbonyl]guanidine, N-[1-(imidazol-4-yl)-1H-pyrrolo[2,3-b]pyridine-3-carbonyl]guanidine, N-[1-(3-(methylsulfonyl)phenyl)-1H-pyrrolo[2,3-b]pyridine-3-carbonyl]guanidine, N-[1-(2-(methylsulfonyl)phenyl)-1H-pyrrolo[2,3-b]pyridine-3-carbonyl]guanidine, N-[1-(2-hydroxyquinolin-4-yl)-1H-pyrrolo[2,3-b]pyridine-3-carbonyl]guanidine, N-[1-(2-methylquinolin-4-yl)-1H-pyrrolo[2,3-b]pyridine-3-carbonyl]guanidine, N-[1-(quinolin-4-yl)-1H-pyrrolo[2,3-b]pyridine-3-carbonyl]guanidine, N-[1-(quinolin-2-yl)-1H-pyrrolo[2,3-b]pyridine-3-carbonyl]guanidine, N-[1-(isoquinolin-1-yl)-1H-pyrrolo[2,3-b]pyridine-3-carbonyl]guanidine, N-[1-(pyridin-2-yl)-1H-pyrrolo[2,3-b]pyridine-3-carbonyl]guanidine, N-[1-(pyridin-4-yl)-1H-pyrrolo[2,3-b]pyridine-3-carbonyl]guanidine, N-[1-(4-(methylsulfonyl)phenyl)-1H-pyrrolo[2,3-b]pyridine-3-carbonyl]guanidine, N-[1-(3-(dimethylamino)phenyl)-1H-pyrrolo[2,3-b]pyridine-3-carbonyl]guanidine, N-[1-(7-methyl-7H-pyrrolo[2,3-d]pyrimidin-4-yl)-1H-pyrrolo[2,3-b]pyridine-3-carbonyl]-guanidine, and N-[1-(2-hydroxy-quinolin-4-yl)-1H-pyrrolo[2,3-b]pyridine-3-carbonyl]-guanidine.

6. The compound of formula I according to claim 5 selected from the group consisting of:

N-[1-(2-hydroxyquinolin-4-yl)-1H-pyrrolo[2,3-b]pyridine-3-carbonyl]guanidine,

N-[1-(2-methylquinolin-4-yl)-1H-pyrrolo[2,3-b]pyridine-3-carbonyl]guanidine,

N-[1-(quinolin-4-yl)-1H-pyrrolo[2,3-b]pyridine-3-carbonyl]guanidine,

N-[1-(quinolin-2-yl)-1H-pyrrolo[2,3-b]pyridine-3-carbonyl]guanidine,

N-[1-(isoquinolin-1-yl)-1H-pyrrolo[2,3-b]pyridine-3-carbonyl]guanidine,

N-[1-(pyridin-2-yl)-1H-pyrrolo[2,3-b]pyridine-3-carbonyl]guanidine,

N-[1-(pyridin-4-yl)-1H-pyrrolo[2,3-b]pyridine-3-carbonyl]guanidine,

N-[1-(4-(methylsulfonyl)phenyl)-1H-pyrrolo[2,3-b]pyridine-3-carbonyl]guanidine,

N-[1-(3-(dimethylamino)phenyl)-1H-pyrrolo[2,3-b]pyridine-3-carbonyl]guanidine,

N-[1-(7-methyl-7H-pyrrolo[2,3-d]pyrimidin-4-yl)-1H-pyrrolo[2,3-b]pyridine-3-carbonyl]-guanidine, and N-[1-(2-hydroxy-quinolin-4-yl)-1H-pyrrolo[2,3-b]pyridine-3-carbonyl]-guanidine.

7. A pharmaceutical composition for human, veterinary or phytoprotective use comprising an effective amount of a compound according to claim 1, or a pharmaceutically acceptable salt thereof, together with pharmaceutically acceptable carriers or additives.

8. A pharmaceutical composition for human, veterinary or phytoprotective use comprising an effective amount of a compound according to claim 1, or a pharmaceutically acceptable salt thereof, together with pharmaceutically acceptable carriers or additives, and further in combination with one or more other pharmacologically active ingredients or medicaments.

9. A process for preparing the compound according to claim 1, comprising reacting a compound of formula II

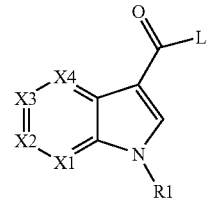

wherein $X_1$, $X_2$, $X_3$, $X_4$ and R1 are as defined in claim 1 and L is a leaving group, with guanidine.

* * * * *